(12) United States Patent
Magilavy et al.

(10) Patent No.: US 8,497,279 B2
(45) Date of Patent: Jul. 30, 2013

(54) TREATMENT FOR DISCOID LUPUS

(75) Inventors: Daniel Magilavy, San Francisco, CA (US); Polly Pine, San Carlos, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/416,748

(22) Filed: Mar. 9, 2012

(65) Prior Publication Data

US 2012/0232106 A1    Sep. 13, 2012

Related U.S. Application Data

(60) Provisional application No. 61/451,531, filed on Mar. 10, 2011.

(51) Int. Cl.
*A61K 31/505* (2006.01)

(52) U.S. Cl.
USPC .......................................................... 514/275

(58) Field of Classification Search
USPC .......................................................... 514/275
See application file for complete search history.

(56) References Cited

U.S. PATENT DOCUMENTS

| | | | |
|---|---|---|---|
| 4,605,556 A | 8/1986 | Sato et al. | |
| 7,491,732 B2 | 2/2009 | Li et al. | |
| 7,812,029 B1 | 10/2010 | Singh et al. | |
| 7,915,273 B2 | 3/2011 | Argade et al. | |
| 8,013,120 B2 | 9/2011 | Du Clos et al. | |
| 8,053,434 B2 | 11/2011 | Ding et al. | |

FOREIGN PATENT DOCUMENTS

WO    WO 2006/133426    12/2006

OTHER PUBLICATIONS

Lee et al. "An Animal Model of Antibody Binding in Cutaneous Lupus," *Arthritis and Rheumatism*, 29(6):782-788 (1986).
Furukawa et al. "Animal models of spontaneous and drug-induced cutaneous lupus erythematosus," *Autoimmunity Reviews*, 4:345-350 (2005).
Rothfield et al. "Lupus erythematosus: systemic and cutaneous manifestations," *Clinics in Dermatology*, 24:348-362 (2006).
Werth "Cutaneous Lupus: Insights into Pathogenesis and Disease Classification," *Bulletin of the NYU Hospital for Joint Disease*, 65(3):200-204 (2007).
Bahjat et al. "An Orally Bioavailable Spleen Tyrosine Kinase Inhibitor Delays Disease Progression and Prolongs Survival in Murine Lupus," *Arthritis & Rheumatism*, 58(5):1433-1444 (2008).
Chang et al. "JAK3 Inhibition Significantly Attenuates Psoriasiform Skin Inflammation in CD18 Mutant PL/J Mice," *The Journal of Immunology*, 183:2183-2192 (2009).
Guiducci et al. "Autoimmune skin inflammation is dependent on plasmacytoid dendritic cell activation by nucleic acids via TLR7 and TLR9," *Journal of Experimental Medicine*, 207:2931-2942 (2010).
Ghoreishi et al. "Cutaneous lupus erythematosus: recent lessons from animal models," *Lupus*, 19:1029-1035 (2010).

*Primary Examiner* — Raymond Henley III
(74) *Attorney, Agent, or Firm* — Klarquist Sparkman, LLP; Travis Young

(57) ABSTRACT

Compounds I and II as well as salts and pharmaceutical compositions containing them are useful for treating diseases and/or disorders of the skin, such as cutaneous lupus, for example acute cutaneous lupus erythematosus, subacute cutaneous lupus erythematosus, or discoid lupus erythematosus. In certain embodiments, the compounds are provided in topical compositions.

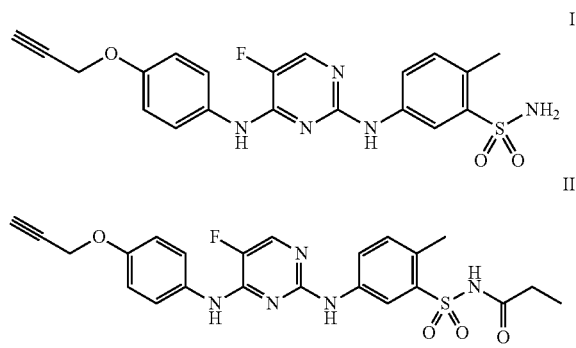

22 Claims, 4 Drawing Sheets

FIG. 4

Cutaneous LE Disease Area and Severity Index (CLASI)

Select the score in each anatomical location that describes the most severely affected cutaneous lupus-associated lesion

| Anatomical Location | activity | | damage | | Anatomical Location |
|---|---|---|---|---|---|
| | Erythema | Scale/ Hypertrophy | Dyspigmentation | Scarring/ Atrophy/ Panniculitis | |
| | 0-absent 1-pink; faint erythema 2- red; 3-dark red; purple/violaceous/ crusted/ hemorrhagic | 0-absent; 1-scale 2-verrucous/ hypertrophic | 0-absent. 1-dyspigmentation | 0 – absent 1 – scarring 2 – severely atrophic scarring or panniculitis | |
| Scalp | | | | See below | Scalp |
| Ears | | | | | Ears |
| Nose (incl. malar area) | | | | | Nose (incl. malar area) |
| Rest of the face | | | | | Rest of the face |
| V-area neck (frontal) | | | | | V-area neck (frontal) |
| Post. Neck &/or shoulders | | | | | Post. Neck &/or shoulders |
| Chest | | | | | Chest |
| Abdomen | | | | | Abdomen |
| Back, buttocks | | | | | Back, buttocks |
| Arms | | | | | Arms |
| Hands | | | | | Hands |
| Legs | | | | | Legs |
| Feet | | | | | Feet |

TREATMENT FOR DISCOID LUPUS

CROSS REFERENCE TO RELATED APPLICATION

This application claims the benefit of U.S. Provisional Application No. 61/451,531, filed Mar. 10, 2011, which is incorporated herein in its entirety.

FIELD

The present disclosure relates to compounds, prodrugs, salts thereof, and pharmaceutical compositions containing them, and methods of using these compounds, prodrugs and compositions thereof in the treatment of dermatological disorders, such as a cutaneous collagen vascular disease, for example a cutaneous lupus disorder, such as discoid lupus erythematosus.

BACKGROUND

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases may be affected by particular cytokine or signaling pathways. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon binding of certain cytokines to their receptors (for example, IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, ocular disorders and diseases, as well as in solid and hematologic malignancies such as leukemia and lymphomas.

Connective tissue disorders are a group of diseases that affect a broad variety of organs, and are sometimes referred to as collagen vascular diseases. This class of diseases includes many distinct inflammatory disorders, such as vasculitis, discoid lupus erythematosus (DLE), systemic lupus erythematosus (SLE), progressive systemic sclerosis, polymyositis/dermatomyositis, polymyalgia rheumatic, polyarteritis nodosa, and Wegener's granulomatosis. These are distinct diseases that have been clinically distinguished from each other for purposes of diagnosis, prognosis, and treatment.

Lupus erythematosus is a generic category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain anti-nuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (eg., DNA-binding test) are almost invariably absent in DLE.

Conventional DLE treatments have included topical corticosteroid ointments or creams, such as triamcinolone acetonide, fluocinolone, flurandrenolide, betamethasone valerate, or betamethasone dipropionate. Resistant plaques can be injected with an intradermal corticosteroid. However, prolonged use of corticosteroids themselves can lead to serious side effects, such as skin atrophy, striae, easy bruising and tearing of the skin, dermatitis, telangiectasia, and increased susceptibility to infection. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL). However, this drug carries the risk of significant retinal toxicity with bull's eye retinopathy. Even after cessation of the drug, visual loss may continue and no medical therapy has been found to reverse the retinal damage.

DLE is a disfiguring disease for which current therapies have proven unsatisfactory. Treatments are also needed for the other cutaneous forms of lupus, such as the acute and sub-acute forms.

SUMMARY

It has now been appreciated that compounds that modulate JAK pathways, and methods of using these compounds, can be used to provide therapeutic benefit to subjects who have cutaneous forms of lupus erythematosus, such as discoid lupus erythematosus (DLE). The compounds may be administered either systemically or topically, but in particular examples the compounds are applied directly to the target cutaneous lesions, for example in a topical formulation. In certain embodiments, the subject has a cutaneous lupus erythematosus, such as DLE, subacute cutaneous lupus, or acute cutaneous lupus. In other examples, the subject has only a cutaneous lupus erythematosus, such as DLE, subacute cutaneous lupus, or acute cutaneous lupus, without any systemic manifestations of lupus. In yet other embodiments, the drug is used to treat cutaneous manifestations of drug-induced lupus erythematosus (DILE).

Disclosed are compounds, prodrugs, corresponding salt forms, and methods of using these compounds, prodrugs and salt forms in the treatment of cutaneous lupus erythematosus, such as a chronic cutaneous lupus erythematosus, such as DLE, or cutaneous manifestations of DILE.

One embodiment provides a compound I, and solvates, prodrugs and pharmaceutically acceptable salts thereof:

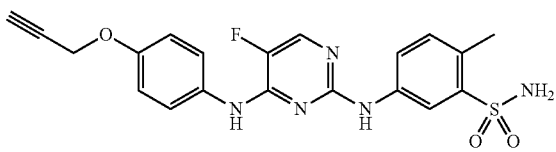

I

Another embodiment provides a particular prodrug of compound I, and pharmaceutically acceptable salt forms thereof, which is compound II:

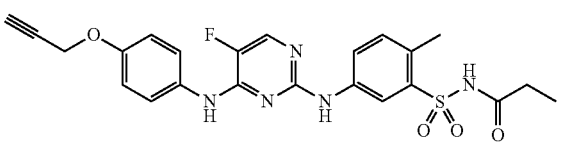

II

In one aspect, the cutaneous lupus erythematosus, such as DLE, is treated using an effective amount of compound I and/or II, as well as salt forms thereof and pharmaceutical compositions which include the compound or compounds. One embodiment provides a method of treating the cutaneous lupus erythematosus by administering to the subject an amount of compound I and/or II effective to treat the condition. In particular examples, the pharmaceutical composition is administered in a topical formulation directly to one or more cutaneous lesions, such as lesions on the skin or mucous membrane (such as on the oral mucosa). In particular examples, the topical formulation is applied directly to the cutaneous lesion without applying it to any substantial amount of unaffected skin.

In one aspect of the disclosed method, administration of one or more of the presently disclosed 2,4-pyrimidinediamine compounds is effective to cause at least partial regression of the lesions that characterize the disease. In some examples, the subject is first determined to have a chronic cutaneous lupus erythematosus such as DLE, and not SLE. For example, the subject displays the clinical and histopathological features of DLE, and does not have anti-double stranded DNA antibodies. In other embodiments, the subject may have both DLE and SLE.

In another aspect, the compound of formula I and/or II, or the pharmaceutically acceptable salt form thereof, is administered either alone or in combination or adjunctively with an anti-inflammatory, an antihistamine, an antibiotic, an antiviral, an emollient, or an analgesic, for example a topical analgesic such as an anesthetic or capsacinoid. In particular examples, the anti-inflammatory agent may be a non-steroidal anti-inflammatory agent (NSAID) or corticosteroid (such as prednisolone), immunosuppressant (such as cyclosporine A), a counterirritant (such as camphor), or an antipruritic (such as crotamiton), administered either systemically (for example orally or parenterally) or topically (for example, in a cream or ointment, or on an adherent topical applicator such as a patch or tape). Alternatively, the compound of formula I and/or II is administered alone or with another biologically active agent in a topical sunscreen agent (to minimize the exposure to ultraviolet light that often worsens DLE). Yet other combination treatments can include the use of concomitant or adjunctive treatment of an associated dermatologic disorder, for example laser or light treatments to reduce facial erythema.

Typically the disclosed compounds of formula I and/or II, when used for treating a cutaneous lupus such as DLE topically, are administered at least once daily, such as at least two, three or four times daily, or are applied to the skin in a sustained release format (such as an adherent dispenser, for example a patch).

In another embodiment, this invention provides a pharmaceutical formulation comprising compound I and/or II, either in parent or salt form, and at least one pharmaceutically acceptable excipient, diluent, preservative, stabilizer, or mixtures thereof.

These and other embodiments are described in more detail below.

BRIEF DESCRIPTION OF THE FIGURES

FIG. 4 is a Table that illustrates the activity and damage of DLE skin lesions, and demonstrates how to rate the severity of DLE. Such ratings are useful in following disease activity and rating response to treatments.

ABBREVIATIONS

Figure 1:
FIG. 1 is a photograph that illustrates some of the disfiguring lesions of DLE as they appear on the extremities.
Figure 1:
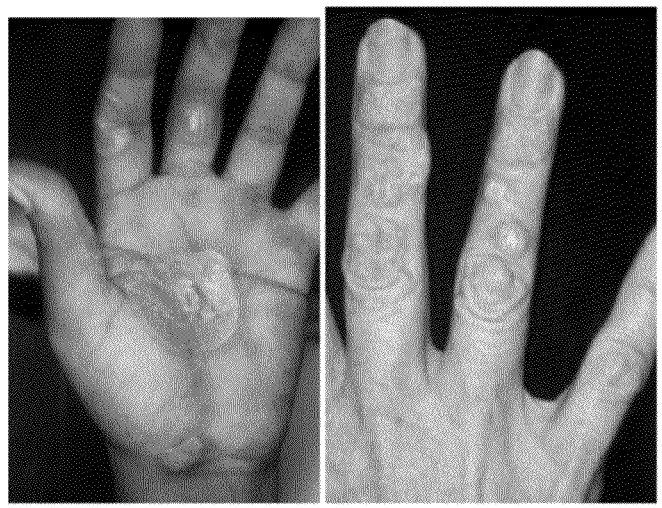
Figure 2:
FIG. 2 is a photograph that illustrates discoid scarring and hypopigmentation on the occipital area of a subject's head.
Figure 3:
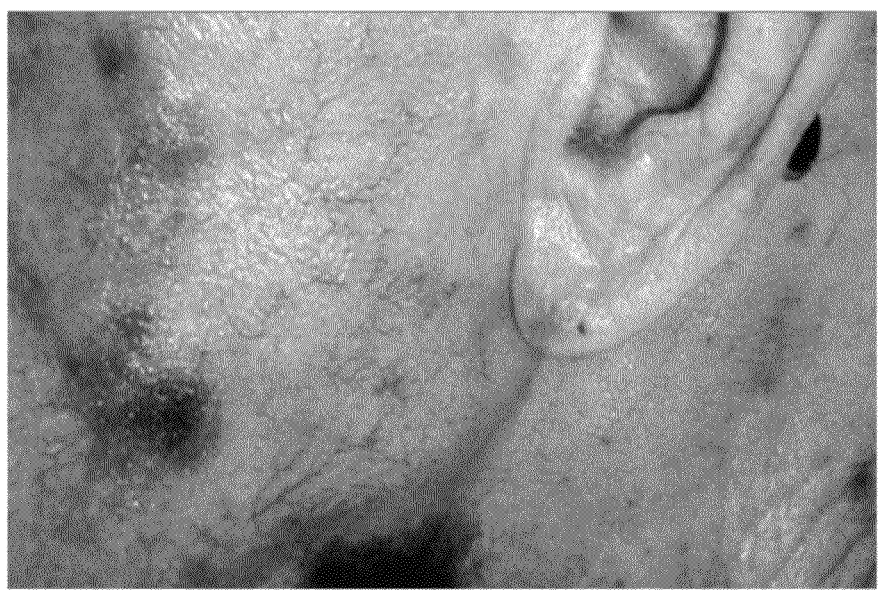
FIG. 3 is a photograph that illustrates the effects of skin atrophy induced by use of a topical glucocorticoid.

ACLE: Acute cutaneous lupus erythematosus
CCLE: Chronic cutaneous lupus erythematosus
COX: Cyclooxygenase
DES: Dry eye syndrome
DILE: Drug induced lupus erythematosus
DLE: Discoid lupus erythematosus
LE: Lupus erythematosus
SCLE: Sub-acute cutaneous lupus erythematosus
SLE: Systemic lupus erythematosus
STAT: Signal transducer and activator of transcription

DETAILED DESCRIPTION

Definitions

As used herein, the following definitions shall apply unless otherwise indicated.

"Corticosteroids" are steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Examples of corticosteroids include cortisol, prednisone and prednisilone. Corticosteroids can be administered either orally, parenterally (for example by injection) or by direct topical application to a lesion on the skin, and they may be combined with the compounds of formula I and/or II in a combination formulation. "Topical corticosteroids" are applied topically directly to the skin, but long term use of topical corticosteroids causes unsightly skin atrophy.

"Cutaneous" or "dermal" refers to the skin, which is the tissue forming the outer covering of the vertebrate body. The skin (which is also sometimes referred to as the "integumentary system"), in combination with the mucous membranes (particularly the oral, nasal, oral and eyelid membranes) help protect the body from its external environment. The skin consists of two layers (the dermis and epidermis), the outermost of which may be covered in many animals (including humans) at least in part with hair. It is mainly protective and sensory in function, along with the mucous membranes of the eye, nose and mouth.

"Cutaneous lupus" or "cutaneous lupus erythematosus" refers to cutaneous manifestations of lupus erythematosus according to the Gilliam classification of lupus erythematosus skin disease. Rothfield et al., Clinics in Dermatology 24:348-362 (2006). This system divides lupus skin disease into lupus erythematosus-specific and lupus erythematosus non-specific skin diseases that show distinctive histologic changes.

"Discoid lupus erythematosus" or "DLE" (also known as chronic cutaneous lupus erythematosus or CCLE) is an often disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. Unlike SLE, antibodies against double-stranded DNA (eg., the DNA-binding test) are almost invariably absent in DLE. In some embodiments of the methods disclosed herein, the compounds of formulas I and II are used to treat double-strand DNA (ds-DNA) negative DLE subjects.

"Chronic cutaneous lupus erythematosus" (CCLE) is generally subdivided into classic discoid lupus erythematosus (DLE), childhood discoid lupus erythematosus, generalized discoid lupus erythematosus, localized discoid lupus erythematosus, lupus erythematosus profundis, lupus erythematosus panniculitis (lupus erythematosus profundus), mucosal lupus erythematosus, tumid lupus erythematosus, chilblain lupus erythematosus, lupus erythematosus-lichen planus overlap syndrome, verrucous lupus erythematosus (hypertrophic lupus erythematosus) and other rare variants. Classic DLE is the most common form of CCLE, and most patients who have classic DLE lesions never develop features of systemic lupus erythematosus. Classic DLE presents as a well-demarcated red-purple macule of a papule with a superficial scale. The lesion increases in size into a coin-shaped, or discoid, plaque with peripheral hyperpigmentation. Adherent scales extend into dilated hair follicles. The center of the lesion becomes depressed with scarring, depigmentation, and telangiectasia. The plaques may become confluent to form large disfiguring lesions. The hair follicle may become plugged with thick scales, which when peeled back reveal keratotic spikes, which is referred to as the carpet tack sign. Histopathological characteristics include hyperkeratosis and follicular plugging, loss of organized basal epidermis and an atrophic spinous layer. The basal layer may also demonstrate edema, liquefaction, basement membrane thickening, increased melanin pigmentation, and pigment incontinence. A mononuclear cell infiltrate of macrophages and T lymphocytes is found in the dermis, with plasma cells in chronic lesions leading to mucin deposition.

"Drug-induced lupus erythematosus" (DILE) is a variant autoimmune disease that occurs as a side-effect of long term use of certain medications. The symptoms of DILE are similar to those of SLE, and can include fatigue, low-grade fever, loss of appetite, muscles aches, arthritis, ulcers of the mouth and nose, facial rash, unusual sensitivity to sunlight, pleuritis, pericarditis, and Raynaud's phenomenon. The ulcers and rash are examples of cutaneous manifestations of DILE. The symptoms resolve within days to months after withdrawal of the culprit drug in a patient who has no underlying immune system dysfunction. The most common drugs that cause DILE are hydralazine, procainamide, quinidine, isoniazid, diltiazem, and minocycline. Some of these drugs (such as procainamide, chlorpromazine, and quinidine) cause the production of antinuclear antibodies against the histone dimer $H2A-H_2B$. Hydralazine forms antinuclear antibodies to H1 and the H3-H4 complex. DILE generally occurs months to years after drug use begins, in contrast to flares of SLE that occur within hours to days after use of a drug begins.

A diagnosis of DILE is made in a patient who has one or more clinical symptoms of SLE (eg, arthralgias, lymphadenopathy, rash, fever); antinuclear antibodies are present; patient had no history of SLE prior to using the culprit drug; suspect drug was taken anytime from 3 weeks to 2 years prior to the appearance of symptoms; and clinical improvement is rapid when the drug is discontinued, while antinuclear antibodies and other serologic markers slowly decrease toward more normal levels.

"Epithelial surfaces" refers to tissue made up of epithelial cells that cover the surfaces of the body. Epithelial surfaces include external surfaces such as the skin and mucosa of the mouth and nose, as well as the linings of internal body surfaces. "External" epithelial surfaces are those exposed to the surfaces of the body (such as the skin, and the lining of the nose and mouth) and that are accessible to direct application of creams or ointments to the surface without the use of instrumentation (such as endoscopes or scalpels).

"Lupus erythematosus" (LE) is a generic term for a collection of autoimmune diseases. Symptoms of LE may affect many different body systems, including joints, skin, kidneys, blood cells, heart and lungs. LE may manifest as a systemic disease (having both cutaneous and other manifestations) or as a purely cutaneous disease (that affects only the skin). The systemic form of LE is known as systemic lupus erythematosus (SLE). Among the cutaneous forms of LE are acute cutaneous lupus erythematosus, subacute cutaneous lupus erythematosus, and chronic cutaneous lupus erythematosus (discoid lupus, discussed above).

Acute cutaneous lupus erythematosus (ACLE) can be either localized or generalized. Localized ACLE is characterized by erythema over the malar eminences of the face and bridge of the nose (butterfly blush) while the nasolabial folds are typically spared. The ACLE rash may have a fine surface scale and be associated with edema, although particularly severe cases can produce vesiculobullous skin changes. Histopathological changes include sparse dermal cellular infiltrate, focal liquefactive degeneration of the basal epidermis, and upper dermal edema. Epidermal necrosis may occur in the most severe forms.

Subacute cutaneous lupus erythematosus (SCLE) is subdivided into two morphological variants: annular SCLE and papulosquamous SCLE. Annular SCLE has also been referred to as lupus marginatus, symmetrical erythema centrifugum, autoimmune annular erythema, and lupus erythematosus gyratum repens. SCLE presents with erythematous macules and papules that subsequently develop into papulosquamous or annular plaques. Most patients will tend to develop predominantly one type of lesion, although some will display the elements of both simultaneously. SCLE is very photosensitive, with lesions most commonly on the neck and upper chest, upper back, shoulders, extensor surfaces of the arms and forearms, and dorsum of the hands (knuckles are typically spared). The face and scalp are uncommonly involved. Histopathological features include hyperkeratosis, degeneration of the basal cell layer, and a mononuclear cell infiltrate in the dermal-epidermal junction and dermis.

"Mucous membranes" (or "mucosa") are linings of mostly endodermal origin, covered in epithelium, which are involved in absorption and secretion. They line cavities that are exposed to the external environment and internal organs. They are continuous with skin at several locations, such as the nostrils, mouth, lips, eyelids, ears, genital area, and anus.

"Non-steroidal anti-inflammatory drug (NSAID)" is a type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate. These agents can be administered either orally, parenterally (for example by injection) or by direct topical application to an inflamed area, and they may be combined with the compounds of formula I and/or II in a combination formulation.

"Pharmaceutically acceptable salt" refers to a biologically compatible salt of a compound that can be used as a drug, which salts are derived from a variety of organic and inorganic counter ions well known in the art.

"Pharmaceutically effective amount" or "therapeutically effective amount" refers to an amount of a compound sufficient to treat a specified disorder or disease or one or more of its symptoms and/or to prevent the occurrence of the disease or disorder. "Treatment" includes arresting further advancement of a disease, as well as reversing the disorder, inducing regression of lesions, or in some examples curing the disorder.

As used herein, the phrase "significantly decreases DLE lesions" means a statistically significant (such as $p<0.05$) decrease in DLE lesions as measured by standard dermatologic practice. For example, a decrease in DLE lesions can be assessed by counting the number of treated lesions, or the total surface area of a treated lesion or lesions.

"Subject" refers to humans and non-human subjects.

"Systemic lupus erythematosus" or "SLE" is an inflammatory autoimmune disorder that occurs predominantly in women, and is characterized variously by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE.

"Topical" delivery refers to application of a drug-containing formulation to the skin to directly treat cutaneous disorders or the cutaneous manifestations of a disease with the intent of substantially directing the pharmacological effect of the drug to the surface of the skin or within the skin. Topical dosage forms are typically semi-solid systems, but can include a variety of other dosage forms such as foams, sprays, medicated powders, solutions and medicated adhesive systems. Topical delivery includes external topical agents that are spread, sprayed, or otherwise dispersed on cutaneous tissues to cover the affected area, or internal topical agents that are applied to the mucous membranes orally, vaginally, or on anorectal tissues for local activity. The topical drugs disclosed herein can be administered in any topical dosage form, for example as a solid (powder, aerosol or plaster); liquid (lotion, liniment, solution, emulsion, suspension, aerosol) or semi-solid (ointment, cream, paste, gel, jelly or suppository).

Compounds

Disclosed are compounds, prodrugs, corresponding salt forms, and methods of using these compounds, prodrugs and salt forms in the treatment of cutaneous LE, such as DLE.

Compounds I and II, as well as their salt forms and pharmaceutical compositions containing them are described in more detail below. Compound I is also referred to as N2-(3-aminosulfonyl-4-methylphenyl)-5-fluoro-N-4-[4-(prop-2-ynyloxy)phenyl]-2,4-pyrimidinediamine. Compound II is also referred to as 5-fluoro-N2-(4-methyl-3-propionylamino-sulfonylphenyl)-N-4-[4-(prop-2-ynyloxy)phenyl]-2,4-pyrimidinediamine.

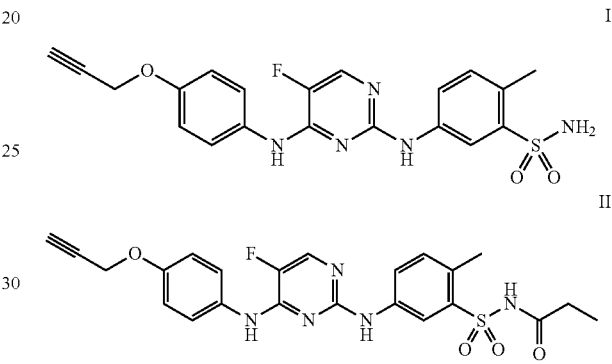

For the purposes of brevity in description, for any embodiment where compound I and compound II are referred to specifically, the embodiment also includes a salt form and/or a pharmaceutical composition containing compound I and/or compound II are used.

One of ordinary skill in the art will appreciate that compound II is a prodrug of compound I, and that compound II need not necessarily be pharmacologically inactive until converted into compound I. The mechanism by which the propionyl progroup metabolizes is not critical, and can be caused by, for example, hydrolysis under the acidic conditions of the stomach, and/or by enzymes present in the digestive tract and/or tissues or organs of the body, for example, esterases, amidases, lipolases, phosphatases including ATPases and kinases, cytochrome P450's of the liver, and the like. In particular embodiments described herein, compounds I and/or II are used to treat dermatological or cutaneous disorders, such as DLE, and may therefore be administered directly to the skin. If an inactive prodrug is administered, it can be activated by eznymes (such as esterases) in the skin, or topically administered with another agent that activates the drug (for example, a reservoir of an activating substance in a patch, or an additional agent that is mixed with the prodrug prior to topical applications). In some embodiments, administration may include not only topical administration but also injection and the like, for example intradermal or intralesional injection. Alternatively, these active agents may be administered systemically.

One of ordinary skill in the art will appreciate that compounds I and II, may exhibit the phenomena of tautomerism, conformational isomerism and/or geometric isomerism. It should be understood that the invention encompasses any tautomeric, conformational isomeric and/or geometric isomeric forms of the compounds as well as mixtures of these various different isomeric forms. Atropisomers are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation about bonds between the 2,4-pyrimidinediamine core structure and groups attached thereto or for example about bonds between the sulfonamide and the phenyl ring to which it is attached. Compounds I and II may be in the form of salts. Such salts include salts suitable for pharmaceutical uses ("pharmaceutically-acceptable salts"), salts suitable for veterinary uses, etc. Such salts may be derived from acids or bases, as is well-known in the art. Exemplary salts described herein are sodium salts, potassium salts, arginine salts, choline salts and calcium salts, but generically any pharmaceutically acceptable salt may be used for methods described herein. Because compound I and compound II have both basic groups, for example pyrimidine nitrogens, and acidic groups, for example acidic protons on the sulfonamide and/or the nitrogens at N2 and N4 of the pyrimidinediamine system, these compounds can form pharmaceutically acceptable acid or base addition salts.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (for example, hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (for example, methanesulfonic acid, ethanesulfonic acid, 1,2-ethane-disulfonic acid, 2-hydroxyethanesulfonic acid, etc.), arylsulfonic acids (for example, benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (for example, an alkali metal ion, an alkaline earth metal ion or an aluminum ion) or coordinates with an organic base (for example, ethanolamine, diethanolamine, triethanolamine, N-methylglucamine, morpholine, piperidine, dimethylamine, diethylamine, triethylamine, ammonia, etc.).

Compounds I and II, as well as the salts thereof, may also be in the form of solvates, for example hydrates, and N-oxides, as are well-known in the art.

Methods

The present invention provides 2,4-substituted pyrimidinediamine compounds I and II, prodrugs, salts and pharmaceutical compositions thereof, for use in treating diseases and/or disorders of the skin and/or mucous membranes, and in particular lesions caused by DLE. In particular, compounds I and II, are administered alone or in combination with other agents. As described, compound I and/or compound II can be administered as the parent and/or the salt form, and as pharmaceutical formulations thereof, and may include activating agents to activate the prodrug compound II to compound I.

As used herein, and as well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Compounds I and II (at least as a source of compound I) are potent, and thus can be administered locally (for example topically or by injection to the skin or mucous membrane) at very low doses, thus minimizing systemic adverse effects. It is believed that this treatment also avoids the side-effects caused by more standard treatments (such as corticosteroids), and is highly effective because of its direct application to affected areas.

Compounds I and II are potent and selective inhibitors of JAKkinases1 and in particular JAK1/3-dependent cytokine signaling operative in T- and B-cells and Syk-dependent signaling in macrophages, dendritic cells, and B-cells. For example, Compound I has a half maximal effective concentration ($EC_{50}$) in human cell based assays against JAK3 and Syk in the range of 0.18 µM and 0.14 µM, respectively, and has little or no activity on other cytokine (IL-1β and TNFα) or receptor tyrosine kinase (RTK) signaling, and is not a broad inhibitor of cell proliferation. Compound I is particularly selective for cytokine signaling pathways containing JAK3. As a consequence of this activity, the compounds may be used in a variety of in vitro, in vivo and ex vivo contexts to regulate or inhibit JAK kinase activity, signaling cascades in which JAK kinases play a role, and the biological responses effected by such signaling cascades. For example, in one embodiment, the compounds may be used to inhibit JAK kinase, either in vitro or in vivo, in virtually any cell type expressing the JAK kinase (such as hematopoietic cells). They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades.

The compounds may also be used in vitro or in vivo to regulate, and in particular inhibit, cellular or biological responses affected by such JAK-dependent signal transduction cascades. Such cellular or biological responses include, but are not limited to, IL-4/ramos CD23 upregulation, IL-2 mediated T-cell proliferation, etc. Importantly, the compounds may be used to inhibit JAK kinases in vivo as a therapeutic approach towards the treatment or prevention of diseases mediated, either wholly or in part, by a JAK kinase activity. Such diseases are referred to as "JAK kinase mediated diseases."

While not wishing to be bound by theory, it is believed that compounds described herein are effective treatments of these cutaneous disorders due, at least in part, to their JAK inhibitory activity. Examples of diseases that are mediated, at least in part, by JAK kinases that can be treated or prevented according to the methods include diseases and disorders of the skin or mucous membranes including, but not limited to, the lesions of cutaneous LE such as DLE, ACLE, SCLE or DILE that are present on the skin and mucous membranes. However, as a result of the aforementioned activities, although methods described herein are directed to treatment of skin and mucous membrane disorders, administration of the compounds and/or formulations may carry other therapeutic benefit, that is, in other tissues or organs of the body. One embodiment is a method of treating a disorder or disease of the skin or mucous membranes (such as DLE, ACLE, SCLE or DILE), where a secondary benefit is also realized. For example, application of the active agents to DLE lesions on the eyelid can also serve as an effective treatment for dry eyes, dry eye syndrome, uveitis, allergic conjunctivitus, glaucoma or rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals. Uveitis or iridocyclitis refers to inflammation of the middle layer of the eye (the "uvea") and in common usage may refer to any inflammatory process involving the interior of the eye. Allergic conjunctivitis is inflammation of the conjunctiva (the membrane covering the white part of the eye) due to allergy. Glaucoma refers to a group of diseases that affect the optic nerve and involves a loss of retinal ganglion cells in a characteristic pattern, i.e., a type of optic neuropathy. Raised intraocular pressure is a significant risk factor for developing glaucoma (above 22 mmHg or 2.9 kPa), and inflammatory processes, e.g uveitis, can cause this rise in intraocular pressure.

The disclosed treatment for DLE, ACLE, SCLE or DILE can also treat the symptoms of rosacea, which is a chronic inflammatory condition characterized by facial erythema that can also affect the eyes and nose (rhinophyma).

In one embodiment, compound I and/or compound II are used to treat any of the aforementioned ocular diseases and/or disorders in combination with treating DLE. In one embodiment, compound I and/or II are employed as salt forms. In a particular embodiment, compound II is used as a salt form. In one embodiment, the salt of compound II is selected from the sodium salt, the potassium salt, the calcium salt, the arginine salt and the choline salt.

Co-Administration

When used to treat lesions of the skin and/or mucous membranes, compounds I and II may be administered singly, as mixtures and/or in combination with other agents useful for activating a prodrug or treating diseases and/or disorders of the skin. Compounds I and II may be administered in mixture or in combination with agents, useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, rituxan, PD4 inhibitors, p38 inhibitors, PDE4 inhibitors, and antihistamines, to name a few. Compounds I and II may be administered per se, in the form of prodrugs, or as pharmaceutical compositions, comprising the active compound and/or prodrug.

The pharmaceutical compositions disclosed herein can be co-administered (concurrently or sequentially) with a variety of other treatments applied to the skin, for example antibacterials (such as BACTROBAN or CLEOCIN); antipsoriasis medications (such as Micanol); antifungal agents (such as LAMISIL, LOTRIMIN, AND NIZORAL); acne treatments (such as benzoyl peroxide topical preparations); treatments for seborrheic dermatitis (such as coal tar); corticosteroids; retinoids (such as Retin-A and Tazorac) which are gels or creams derived from vitamin A that are used to treat conditions including acne; and wart treatments (such as salicylic acid). Any of these agents can be provided in topical or cosmetic formulations, for example in lotions, ointments, creams, gels, soaps, shampoos, or adherent applicators such as patches.

The pharmaceutical compositions disclosed herein can also be co-administered (concurrently or sequentially) with a variety of other treatments that are not applied to the skin, for example treatments that are administered systemically, for example orally or parenterally. Examples of such systemic treatments include other anti-lupus drugs (such as hydroxychloroquine (PLAQUENIL), corticosteroids (such as Prednisone), antibiotics (such as erythromycin, tetracycline, and dicloxacillin), antifungal agents (such as ketoconazole and DIFLUCAN), antiviral agents (such as VALTREX, acyclovir, and FAMVIR), corticosteroids, immunosuppressants (such as CYTOXAN, azathioprine, methotrexate, mycophenolate), and biologics (such as RITUXAN, ENBREL, HUMIRA, REMICADE, STELARA, AND AMEVIVE).

Particular immunosuppressive therapies that can be used in combination with compounds I and II include, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies, for example, antilymphocyte globulin (ALG), antithymocyte globulin (ATG), monoclonal anti-T-cell antibodies (OKT3) and irradiation. These various agents can be used in accordance with their standard or common dosages, as specified in the prescribing information accompanying commercially available forms of the drugs (see also, the prescribing information in the 2006 Edition of *The Physician's Desk Reference*), the disclosures of which are incorporated herein by reference. Azathioprine is currently available from Salix Pharmaceuticals, Inc. under the brand name AZASAN; mercaptopurine is currently available from Gate Pharmaceuticals, Inc. under the brand name PURINETHOL; prednisone and prednisolone are currently available from Roxane Laboratories, Inc.; methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and Abbott under the brand name GENGRAF; IMPDH inhibitors such as mycophenolate mofetil and mycophenolic acid are currently available from Roche under the brand name CELLCEPT and Novartis under the brand name MYFORTIC; azathioprine is currently available from Glaxo Smith Kline under the brand name IMURAN; and antibodies are currently available from Ortho Biotech under the brand name ORTHOCLONE, Novartis under the brand name SIMULECT (basiliximab) and Roche under the brand name ZENAPAX (daclizumab).

In one embodiment, the compound of formula I and/or II, or the pharmaceutically acceptable salt form thereof, is administered either in combination or adjunctively with an ophthalmic formulation of a drug such as an antihistamine, an antibiotic, an anti-inflammatory, an antiviral or a glaucoma medication. Such combination preparations are particularly useful for treating cases of DLE that primarily affect the skin around the eye (such as the eyelids), and may be administered to or around the eye, for example in drops or ointments. When preparing these combination formulations, the compound of formula I and/or II, including the pharmaceutically acceptable salt form thereof, may be combined with ophthalmic antibiotics (such as sulfacetamide, erythromycin, gentamicin, tobramycin, ciprofloxacin or ofloxacin); ophthalmic corticosteroids (such as prednisolone, fluorometholone or dexamethasone; ophthalmic non-steroidal anti-inflammatories (such as ibuprofen, diclofenac, ketorolac or flurbiprofen); ophthalmic antihistamines (such as livostin, patanol, cromolyn, alomide, or pheniramine); ophthalmic antiviral eye medications (such as triflurthymidine, adenine, arabinoside or idoxuridine); ophthalmic glaucoma medications (for example beta-blockers such as timolol, metipranolol, carteolol, betaxolol or levobunolol); ophthalmic prostaglandin analogues (such as latanoprost); ophthalmic cholinergic agonists (such as pilocarpine or carbachol); ophthalmic alpha agonists such as bromonidine or iopidine; ophthalmic carbonic anhydrase inhibitors (such as dorzolamide); and ophthalmic adenergic agonists (such as epinephrine or dipivefrin).

Pharmaceutical Compositions

Pharmaceutical compositions comprising compounds I and II described herein can be manufactured by means of conventional mixing, dissolving, granulating, dragee-making levigating, emulsifying, encapsulating, entrapping or lyophilization processes. The compositions can be formulated in a conventional manner using one or more physiologically acceptable carriers, diluents, excipients or auxiliaries which facilitate processing of the active compounds into preparations which can be used pharmaceutically, and particularly locally or topically.

Compounds I and II can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one embodiment, a pharmaceutical formulation comprises compound I and/or compound II, and at least one pharmaceutically acceptable excipient, diluent, preservative, or stabilizer, or mixtures thereof.

In one embodiment, the compounds are provided as non-toxic pharmaceutically acceptable salts as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds described herein carry an acidic moiety, suitable pharmaceutically acceptable salts thereof may include metal salts such as alkali metal salts, for example sodium or potassium salts; and alkaline earth metal salts, for example calcium or magnesium salts.

The pharmaceutically acceptable salts described herein may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Compounds I and II may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, urethral (for example, urethral suppository) or topical routes of administration (for example, gel, ointment, cream, aerosol, etc.) and may be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds described herein may be effective in humans.

The pharmaceutical compositions for the administration of compounds I and II may conveniently be presented in dosage unit form and may be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation and/or placing it in appropriate packaging. In topical formulations of the disclosed compounds, the formulation is placed in an appropriate container (such as a squeeze-tube with a cap for dispensing ointments and creams). Alternatively, the dispenser may include a device for dispensing unit dosages of the drug (such as a bottle or dropper that dispenses a controlled pre-determined dosage of the drug to a target area). In the pharmaceutical composition the active object compound is included in an amount sufficient to produce the desired therapeutic effect. For example, pharmaceutical compositions described herein may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the JAK-selective compound(s) or prodrug(s) may be formulated as solutions, gels, ointments, creams, suspensions, etc. as are well-known in the art. In addition to being suitable for administration to the skin, the solutions, gels, ointments, creams and suspensions are also well-suited for administration directly to the eye. One embodiment is a pharmaceutical formulation comprising compound I and/or compound II, where the formulation is selected from a solution, a gel, an ointment, a cream and a suspension. In one aspect, such formulations formulated for topical administration include a therapeutically effective amount of a compound I and/or compound II or a pharmaceutically acceptable salt thereof, such as a hydrochloride salt or a besylate salt in the case of compound I and, by way of example, a lysine, choline or arginine salt of compound II. Particular embodiments of formulations for use in the methods described herein include a therapeutically effective amount of the compound, a topical base, an antioxidant, an emollient, and an emulsifier. A person of skill in the art will appreciate that a therapeutically effective amount of the compound may vary, but typically the therapeutically effective amount is from 0.1% to 10% (w/w).

The topical base may comprise polyethylene glycol having a selected molecular weight. Particular embodiments comprise a polyethylene glycol having a molecular weight of from 3000 to 8000 daltons as a topical base.

In certain embodiments, the formulation is an ointment, and may further include a water-miscible solvent, such as a polyalkylene glycol having an average molecular weight of from 200 daltons to 600 daltons. In certain embodiments the water-miscible solvent comprises PEG-400, and even more particularly PEG-400 substantially free of impurities. In certain embodiments, PEG-400 substantially free of impurities comprises less than 65 ppm formaldehyde, less than 10 ppm formaldehyde, or 1 ppm or less formaldehyde.

Topical formulations for use as described herein also can include a penetration enhancer, such as dimethyl isosorbide, propylene glycol, or combinations thereof; an emollient, such as water; a surfactant, such as sorbitan monostearate, a polyethylene glycol monostearate, D-α-tocopheryl polyethylene glycol 1000 succinate, a composition comprising glycol stearate/PEG32 stearate/PEG6 stearate, and combinations of surfactants; an antioxidant, such as butylated hydroxyanisole, butylated hydroxytoluene, ascorbic acid, a tocopherol, and combinations thereof, with particular embodiments comprising butylated hydroxytoluene as an antioxidant; and an optional colorant, such as 0.05% to 0.25% (w/w) caramel colorant.

For particular embodiments the therapeutically effective amount is from 0.1% to 10% (w/w), and the pharmaceutical formulation further comprises: from 15% to 40% (w/w) of a topical base, such as a polyalkylene glycol with an average molecular weight of from 4000 to 5000 daltons; from 25% to 50% (w/w) of a water-miscible solvent, such as a polyalkylene glycol with an average molecular weight of from 300 to 500 daltons; from 10% to 20% (w/w) of a penetration enhancer, such as dimethyl isosorbide; from 3% to 15% (w/w) of an emollient, such as water; from 3% to 9% (w/w) of a surfactant, such as polyethylene glycol monostearate; and from 0.5% to 1.5% (w/w) butylated hydroxytoluene as an antioxidant.

Another embodiment of the pharmaceutical formulation comprises from 0.2% to 6% (w/w) of compound I or a pharmaceutically acceptable salt thereof; 30% to 40% (w/w) polyethylene glycol with an average molecular weight of from 4000 to 5000 daltons; from 30% to 40% (w/w) polyethylene glycol with an average molecular weight of from 300 to 500 daltons; 15% (w/w) dimethyl isosorbide; 3 to 5% (w/w) water; 5% (w/w) polyethylene glycol monostearate; 1% (w/w) butylated hydroxytoluene; and 0.05% caramel.

Yet another embodiment of the pharmaceutical formulation comprises 1% (w/w) compound I; 25% to 40% (w/w) polyethylene glycol with an average molecular weight of 4500 daltons; and 30% to 45% (w/w) polyethylene glycol with an average molecular weight of 400 daltons.

Yet another embodiment of the pharmaceutical formulation comprises 3% (w/w) compound I; 32% (w/w) polyethylene glycol with an average molecular weight of 4500 daltons; and 38% to 42% (w/w) polyethylene glycol with an average molecular weight of 400 daltons.

Yet another embodiment of the pharmaceutical formulation comprises 6% (w/w) compound I; 35% (w/w) polyethylene glycol with an average molecular weight of 4500 daltons; and 33% to 35% (w/w) polyethylene glycol with an average molecular weight of 400 daltons.

In one embodiment, the formulation is a solution. In another embodiment, the formulation is a gel. In another embodiment, the formulation is a suspension. In yet another embodiment, the formulation is a cream or ointment. One embodiment is any of the aforementioned formulations in a kit for topical or local administration. In one embodiment, the formulation is a liquid, for example a homogeneous liquid or a suspension, sold in a bottle which dispenses the formulation as drops or a liquid film (for example from an applicator tip that contacts a target area of the skin to dispense the liquid substantially only on a target area of the skin to be treated). In one embodiment, the formulation is a cream or ointment, sold in a tube which dispenses the formulation to a target area of the skin. In another embodiment, the compound is provided in a viscous liquid (such as carboxylmethylcellulose, hydroxypropylmethycellulose, polyethylene glycol, glycerin, polyvinyl alcohol, or oil containing drops) for rubbing into the skin or instilling in the eye. The formulations may have preservatives or be preservative-free (for example in a single-use container).

For topical use, creams, ointments, jellies, gels, solutions or suspensions, etc., compounds I and II can be used for manufacturing a composition or medicament, including medicaments suitable for topical administration. In certain embodiments, compounds I and II may be formulated for topical administration with polyethylene glycol (PEG). These formulations may optionally comprise additional pharmaceutically acceptable ingredients such as diluents, stabilizers and/or adjuvants. In particular embodiments, the topical formulations are formulated for the treatment of skin diseases and/or disorders, such as cutaneous lupus, for example chronic cutaneous lupus, such as DLE.

Systemic formulations include those designed for administration by injection, for example, subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent or activating agents for activating the prodrug. The formulations for injection may be presented in unit dosage form, for example, in ampules or in multidose containers, and may contain added preservatives. They may also be provided in syringes, for example syringes with needles from injection of the drug into the skin, for example directly into a DLE lesion.

Alternatively, the injectable formulation may be provided in powder form for reconstitution with a suitable vehicle, including but not limited to sterile pyrogen free water, buffer, dextrose solution, etc., before use. The powder can include an activating agent for a prodrug, which activates the prodrug when the powder is solubilized in a vehicle. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art, and include dimethyl sulfoxide (DMSO) and dimethyl isosorbide. However, the penetrants can also be used to improve delivery of the active agents into the skin.

For oral administration, the pharmaceutical compositions may take the form of, for example, lozenges, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate);

lubricants (for example, magnesium stearate, talc or silica); disintegrants (for example, potato starch or sodium starch glycolate); or wetting agents (for example, sodium lauryl sulfate). The tablets may be coated by methods well known in the art with, for example, sugars, films or enteric coatings. Additionally, the pharmaceutical compositions containing the 2,4-substituted pyrmidinediamine as active ingredient or prodrug thereof in a form suitable for oral use, may also include, for example, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient (including prodrug) in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents (for example, corn starch, or alginic acid); binding agents (for example starch, gelatin or acacia); and lubricating agents (for example magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. The pharmaceutical compositions described herein may also be in the form of oil-in-water emulsions.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol, Cremophore™ or fractionated vegetable oils); and preservatives (for example, methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

The active compound(s) or prodrug(s) can be conveniently delivered in the form of an aerosol spray from pressurized packs or a nebulizer with the use of a suitable propellant, for example, dichlorodifluoromethane, trichlorofluoromethane, dichlorotetrafluoroethane, fluorocarbons, carbon dioxide or other suitable gas. When administering a pro-drug, it can be co-delivered and mixed thereby with an activating agent, for example to active compound II to compound I. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. Compounds I and II may also be administered in the form of suppositories for rectal or urethral administration of the drug. In particular embodiments, the compounds may be formulated as urethral suppositories, for example, for use in the treatment of fertility conditions, particularly in males, for example, for the treatment of testicular dysfunction.

According to the invention, 2,4-substituted pyrimidinediamine compounds can be used for manufacturing a composition or medicament, including medicaments suitable for rectal or urethral administration. The invention also relates to methods for manufacturing compositions including 2,4-substituted pyrimidinediamine compounds in a form that is suitable for urethral or rectal administration, including suppositories.

Included among the devices which may be used to administer particular examples of compounds I and II are those well-known in the art, such as, metered dose inhalers, liquid nebulizers, dry powder inhalers, sprayers, foamers, thermal vaporizers, and the like. Other suitable technology for administration of particular 2,4-substituted pyrimidinediamine compounds includes electrohydrodynamic aerosolizers. Sprays, aerosols, sponge-tipped applicators and foam dispensers can be used to administer the compounds, either per se or in formulations, directly to the skin, or by intradermal injection directly into skin lesions of LE, such as DLE lesions.

Typically formulations for skin administration contain a pharmaceutically effective amount of a 2,4-pyrimidinediamine compound disclosed herein, such as from about 0.0001% to about 1.0% or more by weight (w/w). In certain formulations, the pharmaceutically effective amount of the compound is 0.0003% to about 0.1% (w/w), such as from about 0.003% to about 0.5% (w/w), or from about 0.01% to about 0.03% (w/w). In other examples, the compound is present in at least 2%, 3% or 5% (w/w).

In certain examples an ophthalmic composition containing a presently disclosed 2,4-pyrimidinediamine compound for ocular administration includes a tonicity agent, a buffer, or both. In certain examples of ophthalmic compositions the tonicity agent is a simple carbohydrate or a sugar alcohol. As is known to one of ordinary skill in the art, tonicity agents may be used in the present compositions to adjust the tonicity of the composition, preferably to that of normal tears. Examples of suitable tonicity agents include, without limitation sodium chloride, potassium chloride, magnesium chloride, calcium chloride, carbohydrates, such as dextrose, fructose, galactose, polyols, such as sugar alcohols, including by way of example, mannitol, sorbitol, xylitol, lactitol, isomalt, maltitol and combinations thereof. Compositions containing a buffer contain, in some examples, a phosphate, citrate, or both.

The 2,4-substituted pyrimidinediamine compound(s) or prodrug(s) described herein, or compositions thereof, will generally be used in an amount effective to achieve the intended result, for example in an amount effective to treat or prevent the particular condition being treated. The compound (s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from DLE provides therapeutic benefit not only when the underlying dermal lesion is eradicated or ameliorated, but also when the patient reports a decrease in the severity or duration of the symptoms associated with the DLE. Therapeutic benefit also includes halting or slowing the progression of the disease, regardless of whether improvement in symptoms is realized.

For prophylactic administration, the compound may be administered to a patient at risk of developing one of the previously described conditions. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergic reaction in the eyes, such as pollen, in an effort to prevent the individual from developing an allergy.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art. A skilled practitioner will be able to determine the optimal dose for a particular individual. Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in Examples 3 and 4 herein. Similarly, an initial dosage of prodrug for systemic use in animals may be formulated to achieve a circulating blood or serum concentration of the metabolite active compound that is at or above an $IC_{50}$ of the particular compound in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pergamon Press, and the references cited therein.

Initial dosages can also be estimated from in vivo data, using animal models such as those disclosed in Example 9.

Animal models useful for testing the efficacy of compounds to treat or prevent the various diseases described above are well-known in the art. Dosage amounts for systemic administration will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Systemic dosage amount and interval may be adjusted individually to provide plasma levels of the compound(s) which are sufficient to maintain therapeutic or prophylactic effect. For example, the compounds may be administered once per week, several times per week (for example, every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation. In view of the much higher therapeutic index of topical administration to the skin, dosages can be increased beyond general systemic dosages without significant additional concern for side-effects and toxicities.

The foregoing disclosure pertaining to the dosage requirements for the 2,4-substituted pyrimidinediamine compounds is pertinent to dosages required for prodrugs, with the realization, apparent to the skilled artisan, that the amount of prodrug(s) administered will also depend upon a variety of factors, including, for example, the bioavailability of the particular prodrug(s), the conversion rate and efficiency into active drug compound under the selected route of administration, co-administration of an activating agent, etc. Determination of an effective dosage of prodrug(s) for a particular use and mode of administration is well within the capabilities of those skilled in the art.

For topical or ocular administration, effective dosages may be those where no significant systemic circulation of the compounds results from administration to the skin or eye, for example, where a topical formulation is applied directly to a cutaneous lesion and a very localized dose is utilized prior to significant systemic circulation.

Additional compounds that can be substituted for compounds I and II in the disclosed methods are specifically contemplated herein and are described in Argade et al. U.S. Pat. No. 7,491,732, issued Feb. 17, 2009 and US Patent Application Publication No. 2007/0203161, published Aug. 30, 2007, both of which are incorporated herein by reference.

Synthesis of the Compounds

Compounds I and II, as well as salts III-VII, are synthesized as described below or by analogy to the syntheses described below. Alternative syntheses would be appreciated by one of ordinary skill in the art.

EXAMPLE 1

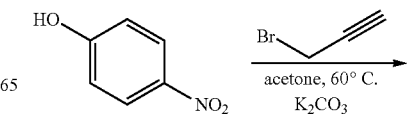

-continued

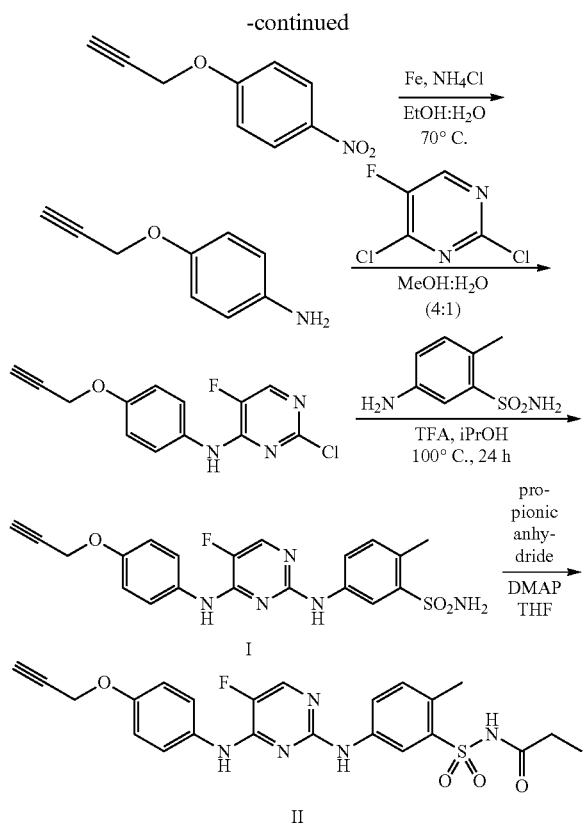

I: N2-(3-Aminosulfonyl-4-methylphenyl)-5-fluoro-N-4-[4-(prop-2-ynyloxy)phenyl]-2,4-pyrimidinediamine 4-Nitrophenol (1.00 g, 7.19 mmol), propargyl bromide (80 wt % in toluene; 0.788 mL, 7.09 mmol), and $K_2CO_3$ (1.08 g, 7.84 mmol) were combined and stirred in acetone (16.0 mL) at 60° C. for 18 h. The reaction mixture was cooled to room temperature and diluted with water (200 mL). 4-(prop-2-ynyloxy)nitrobenzene was isolated as a white solid by suction filtration (1.12 g). $^1$H NMR ($CDCl_3$): δ 8.22 (d, J=9.0 Hz, 2H), 7.05 (d, J=9.0 Hz, 2H), 4.80 (d, J=2.4 Hz, 2H), 2.59 (t, J=2.4 Hz, 1H).

4-(Prop-2-ynyloxy)nitrobenzene (0.910 g, 5.13 mmol), iron (1.42 g, 25.3 mmol), and $NH_4Cl$ (0.719 g, 12.8 mmol) were vigorously stirred in EtOH/water (1:1, 55 mL) at 70° C. for 15 minutes. The reaction mixture was filtered hot through diatomaceous earth and concentrated in vacuo. The residue was suspended in 10% 2N ammoniacal methanol in dichloromethane, sonicated, and filtered through diatomaceous earth. Concentration gave 4-(prop-2-ynyloxy)aniline as an oil which was used without further purification. $^1$H NMR ($CDCl_3$): δ 6.82 (d, J=8.7 Hz, 2H), 6.64 (d, J=8.7 Hz, 2H), 4.61 (d, J=2.4 Hz, 2H), 2.50 (t, J=2.4 Hz, 1H).

4-(prop-2-ynyloxy)aniline (0.750 g, 5.10 mmol) and 2,4-dichloro-5-fluoropyrimidine (1.27 g, 0.760 mmol, commercially available from Sigma-Aldrich of Milwaukee, Wis., USA) were stirred in MeOH/water (4:1, 35 mL) at room temperature for 18 h. The reaction mixture was diluted with EtOAc (200 mL) and washed with 1N HCl (50 mL) and brine (50 mL). The organic layer was dried ($MgSO_4$), filtered and concentrated in vacuo. The residue was purified by column chromatography (silica gel, hexanes ramped to EtOAc:hexanes (1:10)) to provide 2-chloro-5-fluoro-N-4-[4-(prop-2-ynyloxy)phenyl]-4-pyrimidineamine as a light brown solid (0.514 g). $^1$H NMR ($CDCl_3$): δ 8.03 (d, J=2.7 Hz, 1H), 7.53 (d, J=8.7 Hz, 2H), 7.02 (d, J=8.7 Hz, 2H), 6.86 (s, 1H), 4.71 (d, J=2.4 Hz, 2H), 2.55 (t, J=2.4 Hz, 1H); LCMS: purity: 99%; MS (m/e): 279 (MH$^+$).

2-Chloro-5-fluoro-N-4-[4-(prop-2-ynyloxy)phenyl]-4-pyrimidineamine (0.514 g, 1.85 mmol), 3-(aminosulfonyl)-4-methylaniline (0.689 g, 3.70 mmol, made by reduction of commercially available 2-methyl-5-nitrobenzenesulfonamide or synthesized as described below), and trifluoroacetic acid (0.186 mL, 2.41 mmol) were combined with iPrOH (6.0 mL) in a sealed vial and heated at 100° C. for 3 h. The reaction mixture was cooled to room temperature and diluted with 1N HCl (80 mL). N2-(3-Aminosulfonyl-4-methylphenyl)-5-fluoro-N-4-[4-(prop-2-ynyloxy)phenyl]-2,4-pyrimidinediamine (I) was isolated as a white solid by suction filtration (0.703 g). $^1$H NMR (DMSO-$d_6$): δ 10.08 (bs, 2H), 8.19 (d, J=4.5 Hz, 1H), 7.89 (s, 1H), 7.74 (dd, J=2.4 and 8.4 Hz, 1H), 7.58 (d, J=8.7 Hz, 2H), 7.32 (bs, 2H), 7.23 (d, J=8.4 Hz, 1H), 6.97 (d, J=8.4 Hz, 2H), 4.79 (d, J=2.1 Hz, 2H), 3.59-3.55 (m, 1H), 2.53 (s, 3H); LCMS: purity: 97%; MS (m/e): 428 (MH$^+$).

II: 5-fluoro-N2-(4-methyl-3-propionylaminosulfonylphenyl)-N-4-[4-(prop-2-ynyloxy)phenyl]-2,4-pyrimidinediamine N2-(3-Aminosulfonyl-4-methylphenyl)-5-fluoro-N-4-[4-(prop-2-ynyloxy)phenyl]-2,4-pyrimidinediamine, I, (0.200 g, 0.467 mmol), DMAP (40 mg, 0.33 mmol)) and triethylamine (0.118 mL, 0.847 mmol) were stirred in THF (6.0 mL). Propionic anhydride (0.180 mL, 1.40 mmol) was added to the solution drop wise. The reaction mixture was stirred at room temperature overnight. The solution was diluted with ethyl acetate (50 mL) and washed with water (5×25 mL) and brine (10 mL). The organic layer was dried ($MgSO_4$), filtered, and evaporated. The residue was suspended in ethyl acetate (25 mL), sonicated and the solid collected by filtration to give 5-fluoro-N2-(4-methyl-3-propionylaminosulfonylphenyl)-N-4-[4-(prop-2-ynyloxy)phenyl]-2,4-pyrimidinediamine, II, (0.20 g). $^1$H NMR (DMSO-$d_6$): δ 12.01 (s, 1H), 9.44 (s, 1H), 9.26 (s, 1H), 8.16 (d, J=2.4 Hz, 1H), 8.06 (dd, J=0.3 and 3.3 Hz, 1H), 8.00 (dd, J=2.1 and 7.8 Hz, 1H), 7.69 (d, J=8.7 Hz, 2H), 7.19 (d, J=8.4 Hz, 1H), 6.95 (d, J=8.7 Hz, 2H), 4.77 (d, J=2.1 Hz, 2H), 3.56 (t, J=2.1 Hz, 1H), 2.49 (s, 3H), 2.24 (q, J=7.2 Hz, 2H), 0.89 (t, J=7.2 Hz, 3H); LCMS: purity: 98%; MS (m/e): 484 (MH$^+$).

III: 5-fluoro-N2-(4-methyl-3-propionylaminosulfonylphenyl)-N-4-[4-(prop-2-ynyloxy)phenyl]-2,4-pyrimidinediamine mono-sodium salt 5-Fluoro-N2-(4-methyl-3-propionylaminosulfonylphenyl)-N-4-[4-(prop-2-ynyloxy)phenyl]-2,4-pyrimidinediamine, II, (0.125 g, 0.258 mmol) was suspended in acetonitrile (1.5 mL) and water (1.5 mL) and cooled in an ice bath. A solution of 1N NaOH aq. (0.260 mL) was added drop wise. The reaction mixture was stirred until it became clear, filtered through glass wool, and lyophilized to give the sodium salt of II. $^1$H NMR (DMSO-$d_6$): δ 9.17 (bs, 2H), 8.01 (d, J=3.6 Hz, 1H), 7.89 (s, 1H), 7.78-7.69 (m, 3H), 6.99-6.92 (m, 3H), 4.76 (d, J=2.1 Hz, 1H), 2.43 (s, 3H), 1.95 (q, J=7.2 Hz, 2H), 0.86 (t, J=7.2 Hz, 3H); LCMS: purity: 98%; MS (m/e): 484 (MH+).

The following compounds were made in a similar fashion to those above.

IV: 5-Fluoro-N2-[4-methyl-3-(N-propionylaminosulfonyl)phenyl]-N4-[4-(2-propynyloxy)phenyl]-2,4-pyrimidinediamine Potassium Salt $^1$H NMR (DMSO-$d_6$): δ 9.16 (s, 1H), 9.14 (s, 1H), 8.01 (d, J=3.6 Hz, 1H), 7.85 (d, J=2.1 Hz, 1H), 7.75-7.70 (m, 3H), 6.97-6.92 (m, 3H), 4.76 (d, J=1.8 Hz, 2H), 3.55 (t, J=2.4 Hz, 1H), 2.42 (s, 3H), 1.91 (q, J=7.5 Hz, 2H), 0.85 (t, J=7.5 Hz, 3H); LCMS: purity: 97%; MS (m/z): 484 (parent, MH$^+$).

V: 5-Fluoro-N2-[4-methyl-3-(N-propionylaminosulfonyl)phenyl]-N-4-[4-(2-propynyloxy)phenyl]-2,4-pyrimidinediamine Calcium Salt $^1$H NMR (DMSO-d$_6$): δ 9.16 (s, 2H), 8.00 (d, J=3.6 Hz, 1H), 7.88 (d, J=1.8 Hz, 1H), 7.75-7.69 (m, 3H), 6.97-6.92 (m, 3H), 4.76 (d, J=1.8 Hz, 2H), 3.55 (t, J=2.1 Hz, 1H), 2.43 (s, 3H), 1.94 (q, J=7.5 Hz, 2H), 0.87 (t, J=7.5 Hz, 3H); LCMS: purity: 98%; MS (m/z): 484 (parent, MH$^+$).

VI: 5-Fluoro-N2-[4-methyl-3-(N-propionylaminosulfonyl)phenyl]-N4-[4-(2-propynyloxy)phenyl]-2,4-pyrimidinediamine Arginine Salt $^1$H NMR (D$_2$O): δ 7.61 (d, J=3.9 Hz, 1H), 7.57-7.55 (m, 1H), 7.36-7.31 (m, 1H), 7.12 (d, J=8.7 Hz, 2H), 6.88 (d, J=8.7 Hz, 1H), 6.72 (d, J=9.0 Hz, 2H), 4.77-4.75 (m, 2H), 3.60 (t, J=6.0 Hz, 1H), 3.09 (t, J=6.9 Hz, 2H), 2.84-2.81 (m, 1H), 2.35 (s, 3H), 2.03 (q, J=5.7 Hz, 2H), 1.80-1.72 (m, 2H), 1.61-1.48 (m, 2H), 0.855 (t, J=7.5 Hz, 3H); LCMS: purity: 98%; MS (m/z): 484 (parent, MH$^+$).

VII: 5-Fluoro-N2-[4-methyl-3-(N-propionylaminosulfonyl)phenyl]-N4-[4-(2-propynyloxy)phenyl]-2,4-pyrimidinediamine Choline Salt $^1$H NMR (DMSO-d$_6$): δ 9.16 (s, 2H), 8.00 (d, J=3.6 Hz, 1H), 7.85 (d, J=1.8 Hz, 1H), 7.75-7.69 (m, 3H), 6.97-6.90 (m, 3H), 5.27 (t, J=4.8 Hz, 1H), 4.76 (d, J=1.8 Hz, 2H), 3.86-3.77 (m, 2H), 3.56-3.54 (m, 1H), 3.40-3.54 (m, 2H), 3.08 (s, 9H), 2.42 (s, 3H); LCMS: purity: 99%; MS (m/z): 484 (parent, MH$^+$).

Example 2

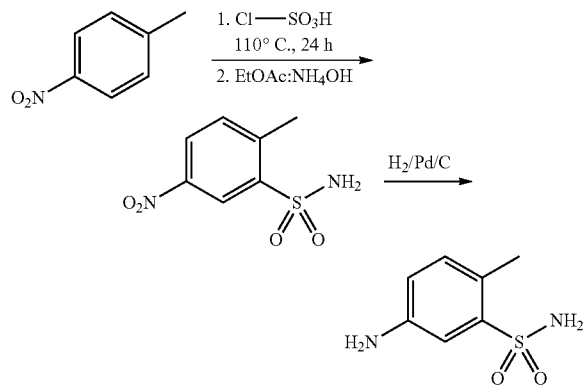

5-amino-2-methylbenzenesulfonamide 4-methylnitrobenzene (20 mmol) is treated at 0° C. with chlorosulfonic acid (5.29 mL, 80 mmol) and then, after bringing the homogeneous solution to room temperature, it was stirred at 110° C. for 24 hours. The resulting slurry was then poured over ice water (100 gm), extracted with diethyl ether (3×75 mL), and the organic phase washed with water (75 mL), then dried over anhydrous sodium sulfate. The solvent was then removed under reduced pressure to afford the crude sulfonyl chloride which was taken up in ethyl acetate and stirred with ammonium hydroxide overnight at room temperature. After the ethyl acetate layer was separated, the aqueous layer was extracted with ethyl acetate. The organic layers were combined, dried over anhydrous sodium sulfate and the solvent was removed under reduced pressure. The oil obtained was purified by column chromatography (silica gel, hexanes then 10%, 20%, up to 50% ethyl acetate in hexanes to afford 3-aminosulfonyl-4-methylnitrobenzene, LCMS: purity: 95%; MS (m/e): 217 (MH+).

To a solution of 3-aminosulfonyl-4-methylnitrobenzene in dichloromethane and methanol was added 10% Pd/C and the mixture shaken under a hydrogen atmosphere at 50 psi for 15 minutes. The mixture was filtered through diatomaceous earth and the filter cake was washed with methanol. The combined organic solvents were concentrated under reduced pressure to give crude product, which was further purified by flash column chromatography (ethyl acetate:hexanes 1:1) to give 3-aminosulfonyl-4-methylaniline, LCMS: purity: 87%; MS (m/e): 187 (MH+).

Example 3

Assay for Ramos B-Cell Line Stimulated with IL-4

One means of assaying for JAK inhibition is detection of the effect of compounds I and II on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (for example, the 2,4-substituted pyrimidinediamine compounds described herein) on the JAK1 and JAK3 kinases, human Ramos B cells are stimulated with human IL-4. Twenty to 24 hours post stimulation, cells are stained for upregulation of CD23 and analyzed using flow cytometry (FACS). A reduction of the amount of CD23 present compared to control conditions indicates the test compound actively inhibits the JAK kinase pathway. An exemplary assay of this type is described in greater detail below.

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells are stimulated with human IL-4.

The Ramos B-cell line was acquired from ATCC (ATCC Catalog No. CRL-1596). The cells were cultured in RPMI 1640 (Cellgro, MediaTech, Inc., Herndon, Va., Cat No. 10-040-CM) with 10% fetal bovine serum (FBS), heat inactivated (JRH Biosciences, Inc, Lenexa, Kans., Cat No. 12106-500M) according to ATCC propagation protocol. Cells were maintained at a density of $3.5 \times 10^5$. The day before the experiment, Ramos B-cells were diluted to $3.5 \times 10^5$ cells/mL to ensure that they were in a logarithmic growth phase.

Cells were spun down and suspended in RPMI with 5% serum. $5 \times 10^4$ cells were used per point in a 96-well tissue culture plate. Cells were pre-incubated with compound or DMSO (Sigma-Aldrich, St. Louis, Mo., Cat No. D2650) vehicle control for 1 hour in a 37° C. incubator. Cells were then stimulated with IL-4 (Peprotech Inc., Rocky Hill, N.J., Cat No. 200-04) for a final concentration of 50 units/mL for 20-24 hours. Cells were then spun down and stained with anti-CD23-PE(BD Pharmingen, San Diego, Calif., Cat No. 555711) and analyzed by FACS. Detection was performed using a BD LSR I System Flow Cytometer, purchased from Becton Dickinson Biosciences of San Jose, Calif. The IC$_{50}$ calculated based on the results of this assay are provided in Table 1.

Example 4

Primary Human T-cell Proliferation Assay Stimulated with IL-2

The JAK activity of the compounds described herein may further be characterized by assaying the effect of compounds I and II described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with compounds I and II in the presence of IL-2 for 72 hours and at the assay endpoint intracellular ATP concentrations are measured to assess cell viability. A reduction in cell proliferation compared to control conditions is indicative of inhibition of the JAK kinase pathway. An exemplary assay of this type is described in greater detail below.

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum:ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 µg)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells were stimulated for 3-4 days, then transferred to a fresh flask and maintained in RPMI with 10% FBS and 40 U/mL IL-2.

Primary T-cells were washed twice with PBS to remove the IL-2 and resuspended in Yssel's medium at $2\times10^6$ cells/mL. 50 µL of cell suspension containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, Mo., Catalog No. D2650) from 5 mM in 3-fold dilutions, and then diluted 1:250 in Yssel's medium. 50 µL of 2x compound was added per well in duplicate and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to room temperature. After mixing the Cell Titer-Glo reagent and diluent together, 100 µL was added to each well. The plates were mixed on an orbital shaker for two minutes to induce lysis and incubated at room temperature for an additional ten minutes to allow the signal to equilibrate. Detection was performed using a Wallac Victor2 1420 multilabel counter purchased from Perkin Elmer, Shelton, Conn. The $IC_{50}$ calculated based on the results of this assay are provided in Table 1.

Example 5

A549 Epithelial Line Stimulated with IFNγ

The JAK activity of the compounds described herein may also be characterized by assaying the effect of compounds I and II described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail below and in Example 6.

A549 lung epithelial cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The A549 lung epithelial carcinoma cell line originated from the American Type Culture Collection. Routine culturing was with F12K media (Mediatech Inc., Lenexa, Kans., Cat. No. 10-025-CV) with 10% fetal bovine serum, 100 I.U. penicillin and 100 ng/mL streptomycin (complete F12k media). Cells were incubated in a humidified atmosphere of 5% $CO_2$ at 37° C. Prior to use in the assay, A549 cells were washed with PBS and trypsinized (Mediatech Inc., Cat. No. 25-052-CI) to lift the cells. The trypsin cell suspension was neutralized with complete F12K media and centrifuged to pellet the cells. The cell pellet was resuspended in complete F12K media at a concentration of $2.0\times10^5$/mL. Cells were seeded at 20,000 per well, 100 µL total volume, in a flat bottom tissue culture plate and allowed to adhere overnight.

On day two, A549 cells were pre-incubated with a 2,4-substituted pyrimidinediamine test compound or DMSO (control) (Sigma-Aldrich, St. Louis, Mo., Catalog No. D2650) for 1 hour. The cells were then stimulated with IFNγ (75 ng/mL) (Peprotech Inc., Rocky Hill, N.J., Cat. No. 300-02) and allowed to incubate for 24 hours. The final test compound dose range was 30 µM to 14 nM in 200 µL F12K media containing 5% FBS, 0.3% DMSO.

On day three, the cell media was removed and the cells were washed with 200 µL PBS (phosphate buffered saline). Each well was trypsinized to dissociate the cells, then neutralized by addition of 200 µL complete F12K media. Cells were pelleted and stained with an APC conjugated mouse anti-human ICAM-1 (CD54) (BD Pharmingen, San Diego, Calif., Catalog #559771) antibody for 20 minutes at 4° C. Cells were washed with ice cold FACS buffer (PBS+2% FBS) and surface ICAM-1 expression was analyzed by flow cytometry. Detection was performed using a BD LSR I System Flow Cytometer, purchased from BD Biosciences of San Jose, Calif. Events were gated for live scatter and the geometric mean was calculated (Becton-Dickinson CellQuest software version 3.3, Franklin Lakes, N.J.). Geometric means were plotted against the compound concentration to generate a dose response curve. The $IC_{50}$ calculated based on the results of this assay are provided in Table 1.

Example 6

U937 IFNγ ICAM1 FACS Assay

U937 human monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The U937 human monocytic cell line was obtained from ATCC of Rockville Md., catalog number CRL-1593.2, and cultured in RPM1-1640 medium containing 10% (v/v) FCS. U937 cells were grown in 10% RPMI. The cells were then plated at a concentration of 100,000 cells per 160 μL in 96 well flat bottom plates. The test compounds were then diluted as follows: 10 mM test compound was diluted 1:5 in DMSO (3 μL 10 mM test compound in 12 μL DMSO), followed by a 1:3 serial dilution of test compound in DMSO (6 μL test compound serially diluted into 12 μL DMSO to give 3-fold dilutions). Then 4 μL of test compound was transferred to 76 μL of 10% RPMI resulting in a 10× solution (100 μM test compound, 5% DMSO). For control wells, 4 μL of DMSO was diluted into 76 μL 10% RPMI.

The assay was performed in duplicate with 8 points (8 3-fold dilution concentrations from 10 μl) and with 4 wells of DMSO only (control wells) under stimulated conditions and 4 wells of DMSO only under unstimulated conditions.

The diluted compound plate was mixed 2× using a multi-mek (Beckman Coulter of Brea, Calif.) and then 20 μL of the diluted compounds was transferred to the 96 well plate containing 160 μL of cells, which were then mixed again twice at low speeds. The cells and compounds were then pre-incubated for 30 minutes at 37° C. with 5% $CO_2$.

The 10× stimulation mix was made by preparing a 100 ng/mL solution of human IFNγ in 10% RPMI. The cells and compound were then stimulated with 20 μL of IFNγ stimulation mix to give a final concentration of 10 ng/mL IFNγ, 10 μM test compound, and 0.5% DMSO. The cells were kept under conditions for stimulation for 18-24 hours at 37° C. with 5% $CO_2$.

The cells were transferred to a 96 well round bottom plate for staining and then kept on ice for the duration of the staining procedure. Cells were spun down at 1000 rpm for 5 minutes at 4° C., following which the supernatant was removed. Following removal of the supernatant, 1 μL APC conjugated mouse anti-human ICAM-1 antibody was added per 100 μL FACS buffer. The cells were then incubated on ice in the dark for 30 minutes. Following incubation, 150 μL of FACS buffer was added and the cells were centrifuged at 1000 rpm for 5 minutes at 4° C., following which the supernatant was removed. After removal of the supernatant, 200 μL of FACS buffer was added and the cells were resuspended. After suspension, the cells were centrifuged at 1000 rpm for 5 min at 4° C. Supernatant was then removed prior to resuspension of the cells in 150 μL FACS buffer.

Detection was performed using a BD LSR I System Flow Cytometer, purchased from BD Biosciences of San Jose, Calif. The live cells were gated for live scatter and the geometric mean of ICAM-APC was measured (Becton-Dickinson CellQuest software version 3.3, Franklin Lakes, N.J.). Both % live cells and ICAM-1 expression was analyzed. The assays for the test compounds were carried out in parallel with a control compound of known activity. The $EC_{50}$ for the control compound is typically 40-100 nM. The $IC_{50}$ calculated based on the results of this assay are provided in Table 1.

TABLE 1

| Compound | Example 3 | Example 4 | Example 5 | Example 6 |
|---|---|---|---|---|
| I | 0.056 | 0.181 | 11.338 | 0.565 |
| II | 9.655 | | | |
| III | 3.972 | | | |
| IV | 2.318 | 5.560 | | |
| V | 0.373 | | | 25.126 |
| VI | 0.104 | 0.262 | 4.973 | 0.424 |
| VII | 0.022 | 0.053 | | 0.140 |

Example 7

Pharmaceutical Formulations

This example describes pharmaceutical formulations containing compound I or II (which will be understood to also include salts thereof). Such formulations are prepared as known to those of skill in the art and additional formulations will be readily apparent to those of skill in the art upon consideration of this Example and additional disclosure herein.

TABLE 2

| Formulation No. | Formulation Components |
|---|---|
| 1 | 50 mM pH 7.4 phosphate buffer, 0.05% Tween 80, 0.5% NaCl |
| 2 | 50 mM pH 7.4 phosphate buffer, 0.36% HPMC, 0.2% glycerin, 1% PEG400, 0.35% NaCl |
| 3 | 5 mM pH 7.4 phosphate buffer, 0.36% HPMC, 0.2% glycerin, 1% PEG400, 5% Cremophor ELP, 4.3% mannitol |
| 4 | 10 mM pH 5.8 citrate buffer, 4.2% mannitol |
| 5 | 10 mM pH 5.8 citrate buffer, 4.2% mannitol, 0.36% HPMC, 0.2% glycerin |
| 6 | 0.3% tyloxapol, 0.5% Carbopol974P, 2.25% mannitol, 50 mM pH 6.5 phosphate buffer, 230 mOsm/kg |
| 7 | 0.3% tyloxapol, 0.1% Carbopol974P, 2.25% mannitol, 50 mM pH 6.5 phosphate buffer, 230 mOsm/kg |

Each of the above formulations, 1-7, are prepared with compound I or II in three dosage concentrations: 0.001%, 0.003% and 0.01% (w/w). Each formulation is prepared by adding the specified amount of a tonicity agent (mannitol) to a flask, heating to about 50° C. in about half the final volume of the specified buffer (phosphate or citrate). After heating, the appropriate amount of compound I or II is added along with the additional excipients (glycerin and/or PEG400) as indicated. Purified water is added in sufficient quantity. The mixture is stirred to homogeneity (about five minutes) and then filtered through a sterilizing filter membrane into a sterile vessel. If necessary, pH is adjusted by addition of 1.0 N NaOH.

Optionally, formulations having a higher concentration of compound I or II (for example, 0.03% w/w) can include a surfactant and optionally a stabilizing polymer. With reference to formulations 6 and 7, preferred surfactants include Triton X114 and tyloxapol, which are commercially available from Sigma-Aldrich (of St. Louis, Mo.) and Pressure Chemical Company (of Pittsburgh, Pa.), respectively. Preferred stabilizing polymers include the carbomer Carbopol 974p (commercially available from Lubrizol, of Wickliffe, Ohio).

Formulations 6 and 7 are prepared by dispersing the carbomer first in the surfactant containing buffer at 10× of their final concentration (e.g. 3% tyloxapol in 50 mM phosphate buffer at pH 6.5 with 2.5% mannitol and 5% Carbomer 974p). Either compound I or compound II is then dispersed in this preconcentrate also at 10× of its final concentration. The mixture is homogenized, with final formulation being obtained by 10× dilution of filtered preconcentrate in a matching buffer.

Methods of formulating and testing the drugs for topical application are described, for example, in Remington, The Science and Practice of Pharmacy ($21^{st}$ edition), pages 872-882 (2006). The drug is formulated for delivery of drug to a desired depth of the skin surface, while avoiding unwanted systemic absorption of the drug. Various penetration enhancers can be added to the composition, such as an alcohol, alkyl methyl sulfoxide, pyrrolidone, laurocapram, dimethyl formamide, tetrahydrofurfuryl alcohol, an amphiphile, or other miscellaneous enhancers such as clofibric acid amide, heyamethylene lauramide, proteolytic enzymes, terpenes or sesquiterpenes. The penetration enhancers improve drug delivery into the skin.

In one specific example of the formulation, a 60:20:20 ethanol:propylene glycol:water system is used with sufficient propylene glycol to maintain 0.5-2% of the active compound.

Common ingredients which may be used to administer the compound in a topical formulation are vehicles, for example hydrophobic vehicles such as hydrocarbons, liquid petrolatum (mineral oil, liquid paraffin, paraffin oil), white petrolatum (petroleum jelly, VASELINE), yellow petrolatum (petroleum jelly), squalane (perhydrosqualene, spinacane), and silicones; silicones such as liquid polydimethylsiloxanes (dimethicone, silastic, medical grade silicone oil), alcohols such as lauryl alcohols (1-dodecanol, dodecyl alcohols), myristyl alcohols (tetradecanol, tetradecyl alcohols), cetyl alcohols (hexadecanol, ethal, palmityl alcohols), stearyl alcohols (stenol, cetosteryl alcohols), oleyl alcohols (ocenol); sterols such as sterol esters; lanolin such as hydrous wool fat, lanum; anhydrous lanolin (such as wool fat, anhydrous lanum, agnin); semi synthetic lanolins; carboxylic acids such as lauric acid, myristic acid, palmitic acid, stearic acid, oleic acid; esters and polyesters, such as cholesterol esters (stearate), ethylene glycol monoesters, propylene glycol monoesters, glyceryl monoesters, glyceryl monostearate, sorbitol monoesters, sorbitain monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, isopropyl palmitate; ethers and polyethers such as polyethylene-polypropylene glycols (pluronics).

Water-miscible vehicles that may be used as co-solvents include polyols and polyglycols such as propylene glycol (1,2-propanediol), glycerin (glycerol), liquid polyethylene glycol, solid polyethylene glycol (hard macrogol, carbowax), 1,2-phenol-hexanetriol, sorbitol solution, esters and polyesters such as polyoxyethylene sorbitain monoesters (stearate-tweens) and polyoxy ethylene sorbitan polyesters (tweens); ethers and polyethers such as polyethylene glycol monocetyl ether (cetomacrogol 1000) and polyethylene-polypropylene glycols (pluronics).

Various structural matrix formers can be added to the composition, for example hydrocarbons such as white petrolatum (petroleum jelly, VASELINE), yellow petrolatum (petroleum jelly), paraffin (paraffin wax, hard paraffin), microcrystalline wax, ceresin (mineral wax, purified ozokerite); silicones such as fumed silica (cab-β-sil), bentonite (colloidal aluminum silicate), and veegum (colloidal magnesium aluminum silicate); polyols and polyglocols such as solid polyethylene glycol (hard macrogol, carbowax); alcohols such as cetyl alcohols (hexadecanol, ethal, palmityl alcohols), stearyl alcohols (stenol, cetosteryl alcohols); sterold and sterol esters such as cholesterol (cholesterin), lanolin, anhydrous lanolin, and semisynthetic lanolin; carboxylic acids such as lauric acid, myristic acid, palmitic acid, stearic acid, oleic acid; and esters or polyesters such as bees wax, white bees wax (bleached bees wax), Carnauba wax, myricin, cholesterol esters (stearate), polyoxyethylene sorbitain, lard or hydrogenated oils.

The compositions may further include suspending, jelling or viscosity inducing agents, for example silicones such as fumed silica (cab-O-sil), bentonite (colloidal aluminium silicate), or veegum (colloidal magnesium aluminium silicate); polycarboxylates, polysulfates or polysaccharides such as agar, alginates, carragen, acacia, tragacanth, methylcellulose, carboxy methylcellulose, hydroxy ethyl cellulose, carboxy vinyl polymer, gelatin, pectin, xanthan, polyacrylic acid.

Some embodiments may include a water-in-oil emulsifier such as a sterol or sterol ester, for example cholesterol (cholesterin), lanolin (hydrous wool fat, lanum), anhydrous lanolin (wool fat, anhydrous lanum, agnin), or semi synthetic lanolin; carboxylic acids such as Na+, K+, ethanolamin salts of lauric acid, myristic acid, palmitic acid, stearic acid, oleic acid, or an ether or polyether such as polyethylene-polypropylene glycols (pluronics). If an oil-in-water (o/w) emulsifier is desired, examples are esters and polyesters such as polyoxyethylene sorbitain monoesters (stearate-tweens), polyoxy ethylene esters (stearate-polyethylene glycol monoesters, Myrj), polyoxy ethylene sorbitan polyesters (tweens); ethers and polyethers such as polyethylene glycol monocetyl ether (cetomacrogol 1000) or polyethylene-polypropylene glycols (pluronics), and others such as sodium lauryl sulfate, borax (sodium borate), ethanolamine, or triethanolamine.

Suitable surfactants for use in the formulations include, but are not limited to, nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Appropriate combinations or mixtures of such surfactants may also be used.

Suitable moisturizers for use in the formulations of the present invention include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations of the present invention include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

The composition may also include preservatives and antimicrobials, such as benzalkonium chloride, benzoic acid, benzyl alcohol, bronopol, chlorhexidine, chlorocresol, imidazolidinyl urea, paraben esters, phenol, phenoxyethanol, potassium sorbate, or sorbic acid; antioxidants such as α-tocopherol, ascorbic acid, ascorbyl palmitate, butylated hydroxyanisole, sodium ascorbate, sodium metabisulfite; chelating agents such as citric acid or edetic acid; buffers such as citric acid and salts, phosphoric acid and salts, $H_3PO_4$/$NaH_2PO_4$, glycine, acetic acid, triethanolamine, or boric acid; humectants such as glycerin (glycerol), propylene glycol (E 1520), glyceryl triacetate (E1518), sorbitol (E420), xylitol and malitol (E965), polydextrose (E1200), quillaia (E999), lactic acid, urea or lithium chloride; and/or a sequestering antioxidant such as citric acid and it salts ethylenediaminetetraacetic acid (Versene, EDTA).

A particular embodiment of the topical treatment may be an ointment, which is a semisolid preparation intended for external application to the skin or mucous membranes. In a specific example, the ointment is based on petrolatum. The ointment does not contain sufficient water to separate into a second phase at room temperature. A water-soluble ointments may be formulated with polyethylene glycol. Ointments are ideal emollients with good skin penetration and adherence to surfaces. The ointment is in a convenient container such as a tube or jars.

Alternatively, the topical dosage form is a cream in which the compounds are dissolved or suspended in water removable or emollient bases. The creams may be either water-in-oil or oil-in-water compositions. Immiscible compounds may be combined by mechanical agitation or heat using wet gum, dry gum, bottle, and beaker methods. In some embodiments, the cream is an oil-in-water emulsion or aqueous microcrystalline dispersion of long chain fatty acids or alcohols that are water washable and more cosmetically and aesthetically acceptable.

In other embodiments, the active ingredients are provided for administration in a paste, which can be considered an ointment into which a high percentage of insoluble solids have been added, for example as much as 50% by weight. The paste is much stiffer than the ointment due to the presence of solids, which form a particulate matrix over and above the ointment structure already present. Ingredients such as starch, zinc oxide, calcium carbonate, and talc are used as the solid phase. Pastes provide a particularly good protective barrier on skin Like ointment, a paste forms an unbroken, relatively water impermeable film on the skin surface; unlike ointment the film is opaque and therefore an effective sun filter. Thus pastes are particularly effective for protecting the skin from ultraviolet radiation that may worsen the condition being treated (such as DLE).

In yet other embodiments, the active agent is provided in a gel, jelly or lotion. Gels are semisolid systems consisting of dispersions of small or large molecules in an aqueous liquid vehicle rendering jelly-like through the addition of gelling agent. Among the gelling agents used are synthetic macromolecules such as carbomer 934, and cellulose derivatives such as carboxymethylcellulose or hydroxypropylmethylcellulose. Gels are compatible with many substances and may contain penetration enhancers to improve delivery into the skin. The gels may be either single phase gels in which the macromolecules are uniformly distributed throughout a liquid with no apparent boundaries between the dispersed macromolecules and the liquid, or double phase gels in which the gel mass consists of floccules of small distinct particles, often referred to as a magmas. A jelly contains a water-soluble base prepared from natural gums such as tragacanth, pectin, alginate, or boroglycerin, or from synthetic derivatives of a natural substance such as methylcellulose or carboxymethylcellulose. A lotion is a clear solution containing 25-50% alcohol, which optionally contains an antiseptic, or mollient. Other optional ingredients that may be added to the lotion are an extract of witchhazel, menthol, glycerin, boric acid, alum, or potassium oxyquinoline.

In another embodiment the compound is applied in a powder, which contains very fine particle sizes that produce large surface area per unit weight to covers a larger surface area of the body and provide light dispersion. Alternatively the compound is applied in a solution, which is a liquid preparations of soluble chemicals dissolved in solvents such as water, alcohol, or propylene glycol. In yet other examples, it is an emulsion, which is a two-phase preparation in which one phase (the dispersed or internal phase) is finely dispersed in the other (continuous or external phase). The dispersed phase can have either a hydrophobic-base (oil-in-water) or aqueous base (water-in-oil). Because there are two incompatible phases in close conjunction, the emulsion would typically contain a physical stabilizing system, such as a surfactant (ionic or nonionic), polymer (nonionic polymers, polyelectrolytes, or biopolymers), or mixtures of thereof.

For embodiments in which the compound is provided in a suspension, the dosage form contains two phases. The continuous or external phase is generally a liquid or semisolid while the disperse or internal phase is made up of particulate matter that is essentially insoluble in, but dispersed throughout, the continuous phase. The insoluble matter may be intended for physiologic action, for example by external coating. Although the suspension system may separate on standing, the rate of settling may be decreased by varying the formulation to retain a sufficiently homogenous composition for at least the period of time necessary to administer the required dose after shaking its container.

The compound may also be administered in an aerosol, which depends on the power of compressed or liquefied gas to expel the contents from the container. Propellants in the container are responsible for developing the proper pressure within the container and it expel the product when the valve is opened and aids in the atomization or foam production of the products. Topical pharmaceuticals aerosols utilize hydrocarbon (propane, butane, and isobutene) and compressed gases such as nitrogen, carbon dioxide, and nitrous oxide.

Any of these dosage forms can contain separate reservoirs of compounds I/II and an adjunct agent (such as an agent for activating compound II to form compound I).

Example 9

Cutaneous Lupus Mouse Model

This example describes the use of mouse models to screen for treatments for cutaneous lupus (such as DLE), including the selection of regimens for treatment, prevention and combination treatments. Animal models are used to test the claimed compounds, as well as combination formulations, such as those described herein. In particular examples, topical formulations that contain compounds I and/or II are applied to the skin of the animal and the therapeutic response is assessed. After the formulations are administered to the animal, the skin is examined for evidence of decreased number or severity of cutaneous lesions.

Although no single animal-based model has been found to ideally mimic DLE, the MRL/lpr mouse strain has been beneficial as a research tool. Transgenic or knock-out forms of these autoimmune mice have been used to explore manifestations of cutaneous lupus. In the MRL/lpr mouse, the lpr mutation results in an alternation in the Fes gene and a defect of apoptosis resulting in abnormal lymphocyte proliferation with abnormal function and auto-antibody production. These animals develop spontaneous lupus-like skin lesions that are common in early life and become progressively more severe as the mice age. Ghoreishi and Dutz, Lupus 19:1029-1035 (2010).

An alternative mouse model is the TCRα-/- mouse treated with fluorouracil and ultraviolet B light irradiation to induce cutaneous lupus lesions. Furukawa and Yoshimasu, Autoimmunity Reviews 4:345-350 (2005).

However, the presently preferred mouse model for demonstrating and testing the efficacy of the currently disclosed treatments is use of the lupus-prone (NZBxNZW)$F_1$ mice, as disclosed in Guiducci et al., Journal of Experimental Medicine 207:2931-2942 (2010), which is incorporated by reference. These lupus-prone mice develop chronic skin lesions resembling human chronic lupus erythematosus after tape stripping.

The lupus-prone (NZBxNZW)$F_1$ mice are available from The Jackson Laboratory, and may be used at 18-22 weeks of age. C57BL/6 and 129 mice are available as controls (for example from Charles River). The dorsal areas of the mice are shaved in a 3×3 cm area, and tape stripping is performed with 10 strokes of duct tape. The skin will show an increase in the number of PDCs and neutrophils, and the abundant cellular infiltrate is accompanied by increased expression of IFN-regulated and proinflammatory genes. Approximately three weeks following tape stripping the mice have prominent epidermal hyperplasia with hyperkeratosis, keratin-filled craters or cysts, dermal fibrosclerosis and degenerative changes of the subcutaneous fat. These changes are similar to those seen in humans with chronic lupus erythematosus.

In the model, the mouse is exposed to the test agent, using different routes, dosages and regimens of administration. In particular examples, the drugs disclosed herein are applied topically to the areas that have been or will be tape stripped. Alternatively, the test drug is administered systemically. The drug is administered one or more times at fixed intervals prior to or following tape stripping (for example, daily following tape stripping or following the appearance of the skin lesions). Drug response can be assessed by measuring such indicia of disease as the number, surface area or appearance of cutaneous lesions. Even if the number or surface area of lesions is not reduced, the severity of the lesions (such as levels of erythema) can be measured in assessing response to the test treatments. Histological analysis of skin specimens is also performed, and are graded from 1 to 3 based on the following criteria: (a) epidermis thickness; (b) degree of ulceration; (c) intraepithelial inflammation; (d) dermal inflammation; and (e) panniculus inflammation. Histological grading is assigned as follows: 0, normal skin architecture, few dermal leukocytes, and regular adnexa; 1: mild inflammation, slight epidermal hyperplasia, and signs of dermal fibroblast proliferation; 2: moderate inflammation, noticeable epidermal hyperplasia (two- to fourfold increase in epithelial thickness) with hyperkeratosis, significant leukocyte/neutrophil-granulocyte dermal infiltrate with few macrophages, moderate fibrosclerosis of the dermis, reduction in the number of adnexa, and slight degenerative changes of the hypodermic adipose tissue; and 3: severe inflammation, marked epihermal hyperplasia (more than fourfold increase in epithelial thickness) with hyperkeratosis, formation of keratin-filled craters and cysts, diffuse discontinuity of the epidermal layer (ulceration), extensive dermal infiltrate with abundant neutrophils and macrophages, pronounced dermal fibrosclerosis, vanishing of adnexa, and evident degenerative changes of the hypodermic adipose tissue. The different parameters are scored and summed to obtain a total disease score. Cellular infiltrates may be processed using flow cytometry.

Example 10

Methods of Treatment and Combination Formulations

Subjects to be treated with the claimed formulations are selected based on a clinical presentation of cutaneous lupus erythematosus, such as DLE, ACLE, SCLE or DILE. This example specifically addresses the treatment of DLE, but a similar method of treatment can be used for other cutaneous forms of lupus, such as ACLE, SCLE or DILE. The claimed compositions are generally applied topically to the DLE lesions on the skin, for example only to the DLE lesions on the skin, although they may also be applied more generally to the skin or administered systemically. Treatment may be continued for at least a week, month, or year, and in some subjects treatment may extend over multiple years, the duration of disease, or the lifetime of the subject.

In particular cases, subjects are selected for concomitant treatment with other pharmaceutical or non-pharmaceutical interventions, such as systemic PLAQUENIL or topical corticosteroid. In other cases the compounds I and/or II are administered with no other treatment for LE or DLE, such as systemic PLAQUENIL or systemic or topical corticosteroid. In other embodiments, the method includes administering the treatment to a subject with DLE who does not have anti-DNA antibodies, for example anti-ds-DNA antibodies.

The subject is selected by making a diagnosis of a cutaneous lupus erythematosus, for example a chronic cutaneous lupus erythematosus, such as DLE. In this particular example, a subject is selected who does not have SLE (for example, by not having anti-ds DNA antibodies or systemic manifestations of SLE such as inflammation of the kidneys, lung, central nervous system, or any organ other than the skin or mucous membranes of the eyes, nose or mouth). In other examples, the subject only has skin manifestations of disease on the surface of the body, and not lesions of any other organ of the body. A therapeutically effective amount of the compound is provided in a topical petrolatum jelly formulation and the formulation is applied directly to cutaneous lupus erythematosus lesions, such as scaling papules on the trunk and extensor surfaces of the extremities and/or scalp. The pharmaceutical formulation is applied to the lesions daily, for example 2-4 times per day for more than one day, for example at least one week. Topical application of the formulation to the lesions is continued until the lesions to which the formulation is applied regress or disappear, or their progression is delayed or stopped.

In other examples, the therapeutic compound is provided in an effective amount in a sunscreen formulation and is applied to the skin prior to exposure to ultraviolet radiation, to protect against exposure to ultraviolet radiation which is often a trigger for the eruption of cutaneous lupus lesions. The sunscreen formulation may contain, for example, an effective amount of PABA or zinc oxide to minimize skin exposure to ultraviolet radiation.

Combination therapies are also provided that combine the compounds of formula I and/or II (which includes salts thereof) with another agent that treats the cutaneous lupus or another condition, such as a condition associated with the dry eyes. Combination formulations for the treatment of cutaneous lupus (such as DLE) include combination formulations that include a topical corticosteroid, such as a Group I, II, III, IV, V, VI or VII corticosteroid, for example any of the following:

Group I (very potent: up to 600 times stronger than hydrocortisone)
 Clobetasol propionate 0.05% (Dermovate)
 Betamethasone dipropionate 0.25% (Diprolene)
 Halobetasol proprionate 0.05% (Ultravate)
 Diflorasone diacetate 0.05% (Psorcon)
Group II
 Fluocinonide 0.05% (Lidex)
 Halcinonide 0.05% (Halog)
 Amcinonide 0.05% (Cyclocort)
 Desoximetasone 0.25% (Topicort)
Group III
 Triamcinolone acetonide 0.5% (Kenalog, Aristocort cream)
 Mometasone furoate 0.1% (Elocon ointment)
 Fluticasone propionate 0.005% (Cutivate)
 Betamethasone dipropionate 0.05% (Diprosone)
Group IV
 Fluocinolone acetonide 0.01-0.2% (Synalar, Synemol, Fluonid)
 Hydrocortisone valerate 0.2% (Westcort)
 Hydrocortisone butyrate 0.1% (Locoid)
 Flurandrenolide 0.05% (Cordran)
 Triamcinolone acetonide 0.1% (Kenalog, Aristocort A ointment)
 Mometasone furoate 0.1% (Elocon cream, lotion)
Group V
 Triamcinolone acetonide 0.1% (Kenalog, Aristocort cream, lotion)
 Fluticasone propionate 0.05% (Cutivate cream)
 Desonide 0.05% (Tridesilon, DesOwen ointment)
 Fluocinolone acetonide 0.025% (Synalar, Synemol cream)
 Hydrocortisone valerate 0.2% (Westcort cream)
Group VI
 Prednicarbate 0.05% (Aclovate cream, ointment)
 Triamcinolone acetonide 0.025% (Aristocort A cream, Kenalog lotion)
 Fluocinolone acetonide 0.01% (Capex shampoo, Dermasmooth)
 Desonide 0.05% (DesOwen cream, lotion)
Group VII
 Hydrocortisone 2.5% (Hytone cream, lotion, ointment)
 Hydrocortisone 1% (Many over-the-counter brands)

In some examples, the subject is diagnosed with a disorder in addition to cutaneous lupus, wherein the additional disorder is not caused by lupus erythematosus, or is not a manifestation of or associated with lupus erythematosus. For example, a subject with cutaneous lupus eyelid lesions may also be diagnosed with dry eyes and the combination therapy is administered to the subject. In one example, the subject is found to have a meibomitis that would be responsive to topical application of corticosteroids, such as a prednisolone acetate ophthalmic suspension 1%. The compounds of formula I and/or II (which includes salts thereof) are suspended in the prednisolone formulation and instilled in or applied to the eye 2 to 4 times a day. In other examples, if the dry eyes are associated with seasonal allergies or other inflammatory conditions, the eye drops are administered with or in a formulation that includes antihistamines (such as pheniramine, emedastine, or azelastine), decongestants (such as tetrahydrozoline hydrochloride or naphazoline), or a non-steroidal anti-inflammatory agent (such as nepafenac or ketorolac), corticosteroids (such as fluorometholone or loteprednol), mast cell stabilizers (such as azelastie, cromal, emedastine, ketotifen, Iodoxamine, nedocromil, olopatadine, or pemirolast). If the dry eyes are associated with an infectious bacterial condition (such a meibomian gland infection or corneal infection) the eye drops are administered with or in a combination formulation can contain appropriate antibiotics (such as ciprofloxacin, erythromycin, gentamicin, ofloxacin, sulfacetamine, tobramycin, or monofloxacin). If the dry eyes are associated with a viral infection, the eye drops are administered with or in a combination formulation with an anti-viral agent such as trifluridine or idoxuridine.

Another example of a combination therapy is a subject who is diagnosed with both cutaneous lupus lesions on the face and/or ocular rosacea after presenting with irritated eyes and facial erythema with telangiectasia. The subject is treated with eye drops that contain the compounds of formula I and/or II, or a topical formulation that is applied to the face, and the subject is also treated with an oral antibiotic, such as a tetracycline antibiotic, such as minocycline. Alternatively the topical composition for treating the cutaneous LE, such as a gel for treating DLE, also contains a topical agent for treating rosacea, such as metronidazole gel.

In another example, the subject presents with cutaneous lupus and another pre-existing autoimmune disorder, and is treated with the topical formulation that contains the compounds of formula I and/or II. The subject is also treated with systemic (for example) oral corticosteroid therapy, such as a tapering dose of prednisolone.

Example 11

Topical Applicators and Dosage Forms

The compositions of the invention may be used in an application device that permits application of the composition to a target site on the skin without applying the composition to non-target site areas of the skin. For example, a device may be employed that allows the composition to be applied without first applying the composition to one's fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The composition may then be topically spread by the spatulas or swabs, or may be expelled from the syringes onto the person's skin.

In one embodiment of the invention, the composition containing the compound and the enhancing agent is provided in an adhesive patch. Some examples of adhesive patches are well known. For example, see U.S. Pat. Nos. Des. 296,006; 6,010,715; 5,591,767; 5,008,110; 5,683,712; 5,948,433; and 5,965,154. Such patches generally have an adhesive layer, which is applied to a person's skin, a depot or reservoir for holding the pharmaceutical agent, and an exterior surface that prevents leakage of the pharmaceutical from the depot. The exterior surface of a patch is typically non-adhesive.

In accordance with the present invention, the compound for treating cutaneous lupus is incorporated into the patch so that the compound remains stable for extended periods of time. The compound may be incorporated into a polymeric matrix that stabilizes it, and permits the compound to diffuse from the matrix and the patch. The compound may also be incorporated into the adhesive layer of the patch so that once the patch is applied to the skin the compound may diffuse on to the skin or even into or through the skin. In accordance with such an embodiment, the adhesive preferably comprises an enhancing agent, as disclosed herein. In one embodiment, the adhesive layer may be heat activated whereby temperatures of about 37 degrees Celsius cause the adhesive to slowly liquefy so that the compound diffuses out of the patch and on to, into, or through the skin. The adhesive may remain tacky when stored at less than 37 degrees Celsius, and once applied to the skin, the adhesive loses its tackiness as it liquefies. The administration of the compound is complete once the patch no longer adheres to the skin.

Alternatively, the compound may be provided in one or more wells or pockets disposed near the surface of the patch that will contact the skin. In one embodiment, the compound is stored in the wells in a dried, or lyophilized state. Storing such patches in a cooled atmosphere (e.g., about 4 degrees Celsius) maintains the stability of the compound. A patch may be removed from the cool atmosphere when needed, and applied to a person's skin where the compound may be solubilized upon mixing with fluid, such as water or saline. The fluid may be provided separately or as a component of the patch. For example, fluid may be provided on a person's skin so that when the patch containing the dried compound interacts with the fluid, the compound is exposed to the fluid and is solubilized. The solubilized compound may then be able to be absorbed by the skin. As another example, the patch may contain one or more wells or pockets to hold fluid in the patch. The fluid may be forced from the wells or pockets to cause the fluid to mix with the dried compound. For example, the fluid may be provided in a pocket in the patch, and in some embodiments contains an agent for enhancing or activating the compound. Pressure exerted on the patch causes the pocket to rupture and release the fluid so that it mixes with the dried compound. The composition containing the compound may thus diffuse out of the patch. In another example, a fluid such as a gel or creams that contains water may be applied to the skin at a target site. The patch containing the dried compound is then applied to the skin where the fluid mixes with the compound and the composition moves out of the patch and on to the skin.

In patches containing wells of dried compound, the wells are sealed so that the compound remains in the wells until the compound is administered. Accordingly, the wells are sealed with a membrane or film that prevents the compound from diffusing from the wells in the compound's dry state, but that permits the compound to diffuse from the wells when it is solubilized. The membrane may either be porous or nonporous. In one embodiment, the membrane comprises cellulose or starch, and more particularly, the membrane may contain polyvinyl alcohol, polyethylene oxide, and hydroxypropyl methyl cellulose. The membrane is thin (ranging in thickness from about 1 µm to about 1 mm) and dissolves upon contacting liquid. Thus, gel or cream placed on the person's skin or fluid directed from a pocket in the patch may contact the cellulose membrane and cause the membrane to dissolve. After dissolving, the fluid mixes with the dried compound and solubilizes the compound. The composition then diffuses out of the patch and on to the subject's skin.

Additionally, the transdermal patch may include a plurality of small needles that extend through the stratum corneum, but do not extend into the dermis to rupture blood vessels. The needles may be between 20 µm and 1 mm long when extending from the dermal surface of the patch. Thus, the needles extend through the stratum corneum, but terminate before the dermis where the capillary beds are located. The needles may be solid or hollow. Hollow needles may have a lumen extending along their length so that the composition can pass from the depot in the patch to the end of the needle in the epidermis. Solid needles may be used to permit the composition to diffuse along the outer surface of the needle into the epidermis.

In use, the topical applicator is adhesively applied to a target area of the skin that has one or more cutaneous lupus lesions, and the applicator is left in place until the compound in the patch is administered to the cutaneous lesion. The topical applicator (such as a patch) provides sustained release of the drug over a prolonged period of time, such as several hours, or even at least a day or longer.

Example 12

Other Dosage Forms and Additives

The topical formulation may be prepared in a variety of forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Suitable emulsifiers for use in the formulations include, but are not limited to, Incroquat Behenyl TMS (behentrimonium methosulfate, cetearyl alcohol), non-ionic emulsifiers like polyoxyethylene oleyl ether, PEG-40 stearate, ceteareth-12 (e.g., Eumulgin B-1 manufactured by Henkel), ceteareth-20 (e.g., Eumulgin B-2 manufactured by Henkel), ceteareth-30, Lanette O (manufactured by Henkel; ceteareth alcohol), glyceryl stearate (e.g., Cutina GMS manufactured by Henkel), PEG-100 stearate, Arlacel 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations/mixtures thereof. In addition, cationic emulsifiers are preferably combined or mixed with non-ionic emulsifiers in order to form stable emulsion product forms containing high strontium salt concentrations.

Suitable secondary active ingredients for use in the formulations include, but are not limited to, alpha hydroxy acids, sunscreens, antiperspirants, anti-acne drugs, vitamins (especially vitamins A and C) and minerals, and various prescription and over-the-counter medications. The compositions disclosed herein can have multiple active ingredients within the same topical formulation, and combinations of active ingredients such as those listed above may be used, as appropriate for the condition or conditions being treated.

Suitable fragrances and colors, such as FD&C Red No. 40 and FD&C Yellow No. 5, may be used in the formulations of the present invention. Other examples of fragrances and colors suitable for use in topical products are known in the art.

Other suitable additional and adjunct ingredients which may be included in the formulations include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

Also, a variety of product types, including cosmetics, may be formulated in each of the forms described above (i.e., solids, creams, lotions, gels, and liquids). For example, cleansers (for face and body), shampoos/conditioners, hair treatments/dyes/perms/straighteners, antiperspirants/deodorants, make-up products, and other facial, hand and body products may be formulated in any of the five major product forms: solids, creams, lotions, gels, or liquids. Common solid form products include cosmetics such as lipsticks, blushes and rouges, makeup products, antiperspirant and deodorant sticks, and cleansers such as bar soap and powder detergents. Other examples of solid form products include lozenges and suppositories for the treatment of cutaneous lupus lesions of the mucous membranes (such as the mouth or anus). Common cream and lotion form products include alpha-hydroxy acid (AHA) products, moisturizing products and sunscreens, shampoos/conditioners and other hair care products, and cosmetics like concealers and foundations. Common gel products include shaving gels and aftershaves. Common liquid form products include anti-acne solutions, aftershaves, gargles/mouthwashes, and toners/bracers/skin conditioners.

Other methodologies and materials for preparing formulations in a variety of forms are also described in Anthony L. L. Hunting (ed.), "A Formulary of Cosmetic Preparations (Vol. 2)—Creams, Lotions and Milks," Micelle Press (England, N.J. 1993). See, for example, Chapter 7, pp. 5-14 (oils and gels); Chapter 8, pp. 15-98 (bases and emulsions); Chapter 9, pp. 101-120 ("all-purpose products"); Chapter 10, pp. 121-184 (cleansing masks, creams, lotions); Chapter 11, pp. 185-208 (foundation, vanishing and day creams); Chapter 12, pp. 209-254 (emollients); Chapter 13, pp. 297-324 (facial treatment products); Chapter 14, pp. 325-380 (hand products); Chapter 15, pp. 381-460 (body and skin creams and lotions); and Chapter 16, pp. 461-484 (baby products); the contents of which are incorporated herein by reference.

Example 12

An Exemplary Topical Formulation

The topical formulation may be prepared in a variety of strengths and using a variety of excipient concentrations as described herein. Table 2 is a list of the excipients used in this example, and without being limited to any particular theory, the function of each excipient.

TABLE 3

List of excipients and their functions

| Excipient | Function |
| --- | --- |
| PEG400, Glycofurol | Solvent |
| PEG8000, PEG4500, PEG3350 | Topical Base |
| Tefose ® 63, Span ®, Myrj ®, TPGS | Surfactant |
| DMI, PG | Penetration enhancer |
| H$_2$O | Emollient |
| BHT | Antioxidant |
| Caramel | Color Additive |

With reference to Table 3, PEG400 employed in working examples was Super Refined Polyethylene Glycol 400, commercially available from Croda Inc., Edison N.J. Likewise, Super Refined dimethyl isosorbide (DMI), also available from Croda Inc. typically was used in these examples.

To prepare the formulations, excipients and compound I was added to a glass container, and heated and/or sonicated at 65° C. to 70° C. to dissolve API completely. The sample is then cooled to room temperature. The ingredients for two exemplary formulations prepared by this method are set forth below in Tables 4 and 5.

TABLE 4

| Component | Grade | Weight % | Weight (g) per kg |
| --- | --- | --- | --- |
| Compound I | GMP | 3.0 | 30 |
| Super Refined Polyethylene Glycol 400 | NF | 39.95 | 399.5 |
| Polyethylene Glycol 4500 | NF | 32.0 | 320 |
| Butylated Hydroxytoluene, Granular | NF | 1.0 | 10 |
| MYRJ S100-PA-SG | — | 5.0 | 50 |
| Super Refined Dimethyl Isosorbide | — | 15.0 | 150 |
| Purified Water | USP | 4.0 | 40 |
| Caramel | NF | 0.05 | 0.5 |
| Total | | 100 | 1000 |

TABLE 5

| Component | Grade | Weight % | Weight (g) per kg |
| --- | --- | --- | --- |
| Compound I | GMP | 6.0 | 60 |
| Super Refined Polyethylene Glycol 400 | NF | 33.95 | 339.5 |
| Polyethylene Glycol 4500 | NF | 35.0 | 350 |
| Butylated Hydroxytoluene, Granular | NF | 1.0 | 10 |
| MYRJ S100-PA-SG | — | 5.0 | 50 |
| Super Refined Dimethyl Isosorbide | — | 15.0 | 150 |
| Purified Water | USP | 4.0 | 40 |
| Caramel | NF | 0.05 | 0.5 |
| Total | | 100 | 1000 |

We claim:

1. A method of treating cutaneous lupus, comprising topically administering to a subject having cutaneous lupus an effective amount of a compound of formula I and/or II, or a pharmaceutically acceptable salt form thereof

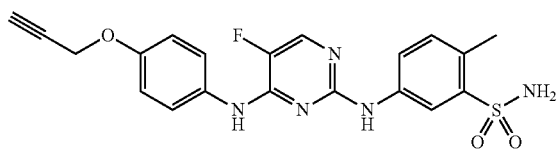

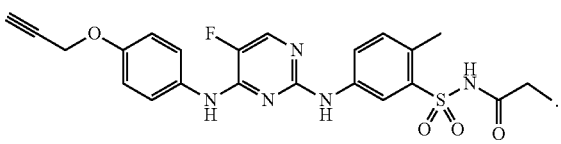

2. The method of claim 1, wherein the subject has cutaneous lupus lesions, and the compound is applied topically to the cutaneous lupus lesions.

3. The method of claim 2, wherein the subject has an acute cutaneous lupus erythematosus, a subacute lupus erythematosus, a chronic cutaneous lupus erythematosus, or a drug induced lupus erythematosus.

4. The method of claim 3, wherein the subject has an acute cutaneous lupus erythematosus or a subacute lupus erythematosus.

5. The method of claim 3, wherein the subject has a chronic cutaneous lupus disorder.

6. The method of claim 5, wherein the chronic cutaneous lupus disorder is discoid lupus erythematosus, chilblain lupus erythematosus, lupus erythematosus-lichen planus overlap syndrome, lupus erythematosus panniculitis, tumid lupus erythematosus, or verrucous lupus erythematosus.

7. The method of claim 6 wherein the discoid lupus erythematosus is a childhood discoid lupus erythematosus, generalized discoid lupus erythematosus, or localized discoid lupus erythematosus.

8. The method of claim 2, wherein the cutaneous lupus comprises a cutaneous lesion associated with drug induced lupus erythematosus.

9. The method of claim 2, wherein the compound is also administered systemically to the subject to treat the cutaneous lupus.

10. The method of claim 1, wherein the pharmaceutically acceptable salt form thereof is a salt of compound II.

11. The method of claim 10, wherein the salt of compound II is selected from the sodium salt, the potassium salt, the calcium salt, the arginine salt and the choline salt.

12. The method of claim 1, wherein the compound of formula I and/or II, or the pharmaceutically acceptable salt form thereof, is administered either in combination or adjunctively with an anti-inflammatory, an antihistamine, an antibiotic, or an antiviral medication.

13. A method of treating a subject for chronic cutaneous lupus erythematosus, comprising administering to the subject an effective amount of a compound of formula I and/or II, or a pharmaceutically acceptable salt form thereof

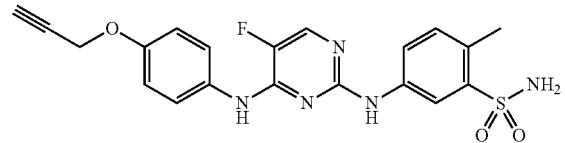

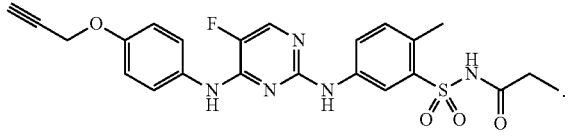

14. The method of claim 13, wherein the subject has an acute cutaneous lupus erythematosus, a subacute lupus erythematosus, or a chronic cutaneous lupus erythematosus.

15. The method of claim 14, wherein the subject has an acute cutaneous lupus erythematosus, or a subacute lupus erythematosus.

16. The method of claim 14, wherein the subject has a chronic cutaneous lupus disorder.

17. The method of claim 16, wherein the chronic cutaneous lupus disorder is discoid lupus erythematosus, chilblain lupus erythematosus, lupus erythematosus-lichen planus overlap syndrome, lupus erythematosus panniculitis, tumid lupus erythematosus, or verrucous lupus erythematosus.

18. The method of claim 17, wherein the chronic cutaneous lupus disorder is discoid lupus erythematosus.

19. The method of claim 18, wherein the subject does not have systemic lupus erythematosus, and does not have anti-DNA antibodies.

20. The method of claim 19, wherein the subject does not have anti-ds-DNA antibodies.

21. The method of claim 1, comprising topically administering to the subject the compound of formula I, or a pharmaceutically acceptable salt form thereof.

22. The method of claim 13, comprising topically administering to the subject the compound of formula I, or a pharmaceutically acceptable salt form thereof.

* * * * *